United States Patent
Wampler et al.

(10) Patent No.: US 12,344,573 B2
(45) Date of Patent: Jul. 1, 2025

(54) SYNTHESIS OF STRAIGHT-CHAIN LEPIDOPTERAN PHEROMONES THROUGH ONE- OR TWO-CARBON HOMOLOGATION OF FATTY ALKENES

(71) Applicant: Provivi, Inc., Santa Monica, CA (US)

(72) Inventors: Keith M. Wampler, Santa Monica, CA (US); Choon Woo Lee, Santa Monica, CA (US); David Rozzell, Burbank, CA (US)

(73) Assignee: Provivi, Inc., Santa Monica, CA (US)

( * ) Notice: Subject to any disclaimer, the term of this patent is extended or adjusted under 35 U.S.C. 154(b) by 1021 days.

(21) Appl. No.: 17/149,662

(22) Filed: Jan. 14, 2021

(65) Prior Publication Data

US 2021/0130270 A1     May 6, 2021

Related U.S. Application Data

(63) Continuation of application No. PCT/US2019/042066, filed on Jul. 16, 2019.

(60) Provisional application No. 62/698,899, filed on Jul. 16, 2018.

(51) Int. Cl.
| | | |
|---|---|---|
| C07C 29/36 | (2006.01) | |
| C07C 45/44 | (2006.01) | |
| C07C 51/09 | (2006.01) | |
| C07C 67/293 | (2006.01) | |
| C07C 67/343 | (2006.01) | |
| C07C 253/30 | (2006.01) | |

(52) U.S. Cl.
CPC .............. *C07C 29/36* (2013.01); *C07C 45/44* (2013.01); *C07C 51/09* (2013.01); *C07C 67/293* (2013.01); *C07C 67/343* (2013.01); *C07C 253/30* (2013.01)

(58) Field of Classification Search
None
See application file for complete search history.

(56) References Cited

U.S. PATENT DOCUMENTS

| | | |
|---|---|---|
| 4,169,105 A | 9/1979 | Syrier |
| 4,254,289 A | 3/1981 | Wall et al. |
| 2017/0137365 A1 | 5/2017 | Wampler et al. |

FOREIGN PATENT DOCUMENTS

| | | |
|---|---|---|
| EP | 0038052 B1 | 3/1984 |
| EP | 0337862 A1 | 10/1989 |
| WO | 2011092467 A1 | 8/2011 |

OTHER PUBLICATIONS

Taber. Tetrahedron Letters, 2009, 50, 2462-2463 (Year: 2009).*
Guldbrandt. Chirality, 2002, 14, 351-363 (Year: 2002).*
Manabe. Synlett, 2012, 23, 1213-1216 (Year: 2012).*
Zeng. Organic Letters, 2002, 4(5), 703-706 (Year: 2002).*
Bouyssi et al., "Formation of Cyclohexanes in the Palladium Catalyzed Reaction of Σ-Unsaturated Cyano Esters and Congeners," Tetrahedron Letters, vol. 36, No. 44, 1995, pp. 8019-8022.
Application No. EP19838403.4, Extended European Search Report, Mailed Aug. 24, 2021, 7 pages.
Kaga et al., "A General and Stereoselective Synthesis of the Capsaicinoids via the Orthoester Claisen Rearrangement," Tetrahedron, vol. 52, No. 25, 1996, pp. 8451-8470.
Application No. PCT/US2019/042066, International Preliminary Report on Patentability, Mailed Jan. 28, 2021, 7 pages.
Application No. PCT/US2019/042066, International Search Report and Written Opinion, Mailed Oct. 24, 2019, 16 pages.

* cited by examiner

*Primary Examiner* — Noble E Jarrell
(74) *Attorney, Agent, or Firm* — Kilpatrick Townsend & Stockton LLP

(57) ABSTRACT

Methods for the preparation of alkenes including insect pheromones are described. The methods include homologation reactions employing reagents such as 1,3-diesters, epoxides, cyanoacetates, and cyanide salts for elongation of starting materials and intermediates by one or two carbon atoms. The alkenes include insect pheromones useful in a number of agricultural applications.

18 Claims, No Drawings

SYNTHESIS OF STRAIGHT-CHAIN LEPIDOPTERAN PHEROMONES THROUGH ONE- OR TWO-CARBON HOMOLOGATION OF FATTY ALKENES

CROSS-REFERENCES TO RELATED APPLICATIONS

The present application is a continuation of International Pat. Appl. No. PCT/US2019/042066, filed on Jul. 16, 2019, which claims priority to U.S. Provisional Pat. Appl. No. 62/698,899, filed on Jul. 16, 2018, which applications are incorporated herein by reference in their entirety.

BACKGROUND OF THE INVENTION

Insect infestation is a primary cause of crop loss throughout the United States. A wide variety of chemical pesticides has been relied upon in the past to control insect pests. However, environmental concerns as well as consumer safety concerns have led to the de-registration of many pesticides and a reluctance to use others on agricultural products which are ultimately consumed as food. As a consequence, there is a desire for the development of alternative biological control agents.

Pheromones are chemicals which are secreted outside the body of insects and can be classified according to the type of behavioral reaction they induce. Pheromone classes include aggregation pheromones, sexual pheromones, trail pheromones, and alarm pheromones. Sex pheromones, for example, are typically secreted by insects to attract partners for mating.

When pheromones are dispersed on leaves of a crop plant, or in an orchard environment in small quantities over a continuous period of time, pheromone levels reach thresholds that can modify insect behavior. Maintenance of pheromone levels at or above such thresholds can impact insect reproductive processes and reduce mating. Use of pheromones in conjunction with conventional insecticides can therefore reduce the quantity of insecticide required for effective control and can specifically target pest insects while preserving beneficial insect populations. These advantages can reduce risks to humans and the environment and lower overall insect control costs. Despite these advantages, pheromones are not widely employed today because of the high cost of synthesizing these compounds for use as active ingredients in agricultural products. Even though thousands of insect pheromones have been identified, less than about twenty insect pests worldwide are currently controlled using pheromone strategies, and only 0.05% of global agricultural land employs pheromones.

BRIEF SUMMARY OF THE INVENTION

Provided herein are methods for the preparation of a $C_6$-$C_{18}$ alkene product. The methods include contacting a $C_4$-$C_{17}$ alkene reactant with a homologation reagent under conditions sufficient to form the $C_6$-$C_{18}$ alkene product.

In some embodiments, the $C_4$-$C_{17}$ alkene reactant is an alkenyl halide or an alkenyl sulfonate, the homologation reagent is a 1,3-diester, and the $C_6$-$C_{18}$ alkene product is a 2-(alkenyl)malonate.

In some embodiments, the $C_4$-$C_{17}$ alkene reactant is an alkenyl halide or an alkenyl sulfonate, the homologation reagent is a cyanoacetate, and the $C_6$-$C_{18}$ alkene product is an alkyl (2-cyano)alkenoate.

In some embodiments, the $C_4$-$C_{17}$ alkene reactant is an alkenyl sulfonate or an alkenyl halide, the homologation reagent is a cyanide salt, and the $C_6$-$C_{18}$ alkene product is an alkenyl nitrile.

In some embodiments, the $C_4$-$C_{17}$ alkene reactant is an alkenyl Grignard reagent, the homologation reagent is an epoxide, and the $C_6$-$C_{18}$ alkene product is an alkenol.

In some embodiments, the $C_4$-$C_{17}$ alkene reactant is an alkenyl Grignard reagent, the homologation reagent is an orthoester or a haloacetal, and the $C_6$-$C_{18}$ alkene product is an alkenal.

In some embodiments, the $C_4$-$C_{17}$ alkene reactant is an alkenyl Grignard reagent, the homologation reagent is a haloalkyl ether, and the $C_6$-$C_{18}$ alkene product is an alkenyl ether.

In some embodiments, the $C_4$-$C_{17}$ alkene reactant is an alkenyl Grignard reagent, the homologation reagent is formaldehyde or a formaldehyde precursor, and the $C_6$-$C_{18}$ alkene product is an alkenol.

A number of pheromones and pheromone precursors, including unsaturated fatty alcohols, unsaturated fatty alcohol acetates, unsaturated fatty aldehydes, unsaturated fatty acid esters, and polyenes, can be synthesized using the methods of the invention.

DETAILED DESCRIPTION OF THE INVENTION

Provided herein are methods for the synthesis of straight-chain lepidopteran pheromones (SCLPs) via synthetic routes that include one- or two-carbon homologation reactions. Using the methods, straight-chain starting materials and intermediates may be lengthened, or homologated, to afford the corresponding $C_{n+1}H_{m+2}$ congener or $C_{n+2}H_{m+4}$ congener. A number of alkene products can be prepared according to the methods of the present disclosure, including products which would otherwise be challenging to synthesize from readily available alkene starting materials.

I. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having," "contains," "containing," or any other variation thereof, are intended to cover a non-exclusive inclusion. A method, process, composition, mixture, article, or apparatus that comprises a list of elements is not necessarily limited to only those elements but may include other elements not expressly listed or inherent to such method, process, composition, mixture, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X, or from 0.98X to 1.02X, or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.99X."

As used herein, the term "pheromone" refers to a substance, or characteristic mixture of substances, that is secreted and released by an organism and detected by a second organism of the same species or a closely related species. Typically, detection of the pheromone by the second organism promotes a specific response, such as a definite behavioral reaction or a developmental process. Insect pheromones, for example, can influence behaviors such as mating and aggregation. Examples of pheromones include, but are not limited to, compounds produced by Lepidoptera (i.e., moths and butterflies belonging to the Geometridae, Noctuidae, Arctiidae, and Lymantriidae families) such as $C_{10}$-$C_{18}$ acetates, $C_{10}$-$C_{18}$ alcohols, $C_{10}$-$C_{18}$ aldehydes, and $C_{17}$-$C_{23}$ polyenes. An "unsaturated pheromone" refers to any pheromone having at least one carbon-carbon double bond.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the terms "olefin" and "alkene" refer to a straight-chain or branched hydrocarbon compound containing at least one carbon-carbon double bond and derivatives thereof. The olefin can be unsubstituted or substituted with one or more functional groups including but not limited to alcohol groups, protected alcohol groups, aldehyde groups, carboxylate groups, and carboxylic acid ester groups. As used herein, the term "olefin" encompasses hydrocarbons having more than one carbon-carbon double bond (e.g., di-olefins, tri-olefins, etc.). Hydrocarbons having more than one carbon-carbon double bond and derivatives thereof are also referred to as "polyenes." The term "fatty olefin" refers to an olefin (e.g., an unsaturated alcohol, an unsaturated carboxylic acid, or an unsaturated carboxylic acid ester), having at least four carbon atoms in the olefin carbon chain; fatty olefins can have, for example, 4, 5, 6, 7, 8, 9, 10, 11, 12, 13, 14, 15, 16, 17, 18, 19, 20, 21, 22, 23, 24, 25, 26, 27, or 28 carbon atoms.

As used herein, the term "metathesis reaction" refers to a catalytic reaction which involves the interchange of alkylidene units (i.e., $R_2C=$units) among compounds containing one or more carbon-carbon double bonds (e.g., olefinic compounds) via the formation and cleavage of the carbon-carbon double bonds. Metathesis can occur between two molecules having the same structure (often referred to as self-metathesis) and/or between two molecules having different structures (often referred to as cross-metathesis). The term "metathesis reaction partner" refers to a compound having a carbon-carbon double bond that can react with an olefin in a metathesis reaction to form a new carbon-carbon double bond.

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction. A "tungsten catalyst" refers to a metathesis catalyst having one or more tungsten atoms. A "molybdenum catalyst" refers to a metathesis catalyst having one or more molybdenum atoms. A "ruthenium catalyst" refers to a metathesis catalyst having one or more ruthenium atoms.

As used herein, the term "metathesis product" refers to an olefin containing at least one double bond, the bond being formed via a metathesis reaction.

As used herein, the term "converting" refers to reacting a starting material with at least one reagent to form an intermediate species or a product. The converting can also include reacting an intermediate with at least one reagent to form a further intermediate species or a product.

As used herein, the term "oxidizing" refers to the transfer of electron density from a substrate compound to an oxidizing agent. The electron density transfer typically occurs via a process including addition of oxygen to the substrate compound or removal of hydrogen from the substrate compound. The term "oxidizing agent" refers to a reagent which can accept electron density from the substrate compound. Examples of oxidizing agents include, but are not limited to, pyridinium chlorochromate, o-iodoxybenzoic acid, and 2,2,6,6-tetramethylpiperidine 1-oxyl.

As used herein, the term "reducing" refers to the transfer of electron density from a reducing agent to a substrate compound. The electron density transfer typically occurs via a process including addition of hydrogen to the substrate compound. The term "reducing agent" refers to a reagent which can donate electron density to the substrate compound. Examples of reducing agents include, but are not limited to, sodium borohydride and sodium triacetoxyborohydride.

As used herein, the term "acylating" refers to converting a alcohol group (—OH), to and ester group (—OC(O)R, where R is an alkyl group as described below).

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycloaliphatic" (or "carbocycle") refers to a monocyclic $C_3$-$C_6$ hydrocarbon, or a $C_5$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl. The term "heteroaliphatic" refers to an aliphatic group wherein at least one carbon atom of the aliphatic group is replaced with a heteroatom (i.e., nitrogen, oxygen, or sulfur, including any oxidized form of nitrogen or sulfur, and any quaternized form of a basic nitrogen).

As used herein, the term "alkyl" is given its ordinary meaning in the art and includes straight-chain alkyl groups and branched-chain alkyl groups. In certain embodiments, a straight chain or branched chain alkyl has about 1-30 carbon atoms in its backbone (e.g., $C_1$-$C_{30}$ for straight chain, $C_3$-$C_{30}$ for branched chain), and alternatively, about 1-20. In some embodiments, an alkyl group may be a lower alkyl group, wherein a lower alkyl group comprises 1-4 carbon atoms (e.g., $C_1$-$C_4$ for straight chain lower alkyls).

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, and the like.

As used herein, the term "alkoxy" refers to a moiety —OR wherein R is an alkyl group as defined above. The term "silylalkyl" refers to an alkyl group as defined herein wherein as least one carbon atom is replaced with a silicon atom. The term "silyloxy" refers to a moiety —$OSiR_3$, wherein each R is independently selected from the group consisting of hydrogen, alkyl, substituted alkyl, aryl, and substituted aryl as described herein.

As used herein, the term "cycloalkyl" refers to a saturated, monocyclic hydrocarbon, bicyclic hydrocarbon, or tricyclic hydrocarbon group that has a single point of attachment to the rest of the molecule. Cycloalkyl groups include alkyl substituted cycloalkyl groups and cycloalkyl substituted alkyl groups. In some embodiments, cycloalkyl rings have from about 3-10 carbon atoms in their ring structure where such rings are monocyclic or bicyclic, and alternatively about 5, 6 or 7 carbons in the ring structure.

As used herein, the term "alkenyl" refers to an alkyl group, as defined herein, having one or more carbon-carbon double bonds. The term "heteroalkenyl" refers to an alkenyl group wherein one or more carbon atoms is replaced with a heteroatom (i.e., nitrogen, oxygen, or sulfur, including any oxidized form of nitrogen or sulfur, and any quaternized form of a basic nitrogen).

As used herein, the term "alkenol" refers to a compound having a formula R—OR' wherein R is an alkenyl group and R' is hydrogen or an alcohol protecting group.

As used herein, the term "alkynyl" refers to an alkyl group, as defined herein, having one or more carbon-carbon triple bonds.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more heteroatoms (e.g., one to four heteroatoms), as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The terms "halogen" and "halo" are used interchangeably to refer to F, Cl, Br, or I.

The term "sulfonate" refers to a moiety —OS(O)$_2$R, wherein R is an substituted alkyl group, a substituted alkyl group, an unsubstituted aryl group, or a substituted aryl group. Examples of sulfonates include, but are not limited to, mesylate (methanesulfonate), triflate (trifluoromethanesulfonate), besylate (benzenesulfonate), tosylate (p-toluenesulfonate), and brosylate (4-bromobenzenesulfonate).

As used herein, the term "Grignard moiety" refers to an organomagnesium halide group. The term "Grignard reagent" refers to a compound containing a Grignard moiety.

As used herein, the term "protecting group" refers to a chemical moiety that renders a functional group unreactive, but is also removable so as to restore the reactivity of the functional group. Examples of "alcohol protecting groups" include, but are not limited to, benzyl; tert-butyl; trityl; tert-butyldimethylsilyl (TBDMS; TBS); 4,5-dimethoxy-2-nitrobenzyloxycarbonyl (Dmnb); propargyloxycarbonyl (Poc); and the like. Examples of "amine protecting groups" include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other alcohol protecting groups and amine protecting groups are known to those of skill in the art including, for example, those described by Green and Wuts (*Protective Groups in Organic Synthesis*, 4$^{th}$ Ed. 2007, Wiley-Interscience, New York).

In some embodiments, alkene reactants, alkene products, homologation reagents, and other compounds may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\alpha$; —(CH$_2$)$_{0-4}$OR$^\alpha$; —O(CH$_2$)$_{0-4}$R$^\alpha$, —O—(CH$_2$)$_{0-4}$C(O)OR$^\alpha$; —(CH$_2$)$_{0-4}$CH(OR$^\alpha$)$_2$; —(CH$_2$)$_{0-4}$SR$^\alpha$; —(CH$_2$)$_{0-4}$Ph, which may be substituted with R$^\alpha$; —(CH$_2$)$_{0-4}$O(CH$_2$)$_{0-1}$Ph which may be substituted with R$^\alpha$; —CH═CHPh, which may be substituted with R$^\alpha$; —(CH$_2$)$_{0-4}$O(CH$_2$)$_{0-1}$-pyridyl which may be substituted with R$^\alpha$; —NO$_2$; —CN; —N$_3$; —(CH$_2$)$_{0-4}$N(R$^\alpha$)$_2$; —(CH$_2$)$_{0-4}$N(R$^\alpha$)C(O)R$^\alpha$; —N(R$^\alpha$)C(S)R$^\alpha$; —(CH$_2$)$_{0-4}$N(R$^\alpha$)C(O)NR$^\alpha$$_2$; —N(R$^\alpha$)C(S)NR$^\alpha$$_2$; —(CH$_2$)$_{0-4}$N(R$^\alpha$)C(O)OR$^\alpha$; —N(R$^\alpha$)N(R$^\alpha$)C(O)R$^\alpha$; —N(R$^\alpha$)N(R$^\alpha$)C(O)NR$^\alpha$$_2$; —N(R$^\alpha$)N(R$^\alpha$)C(O)OR$^\alpha$; —(CH$_2$)$_{0-4}$C(O)R$^\alpha$; —C(S)R$^\alpha$; —(CH$_2$)$_{0-4}$C(O)OR$^\alpha$; —(CH$_2$)$_{0-4}$C(O)SR$^\alpha$; —(CH$_2$)$_{0-4}$C(O)OSiR$^\alpha$$_3$; —(CH$_2$)$_{0-4}$OC(O)R$^\alpha$; —OC(O)(CH$_2$)$_{0-4}$SR—SC(S)SR$^\alpha$; —(CH$_2$)$_{0-4}$SC(O)R$^\alpha$; —(CH$_2$)$_{0-4}$C(O)NR$^\alpha$$_2$; —C(S)NR$^\alpha$$_2$, —C(S)SR$^\alpha$; —SC(S)SR$^\alpha$, —(CH$_2$)$_{0-4}$OC(O)NR$^\alpha$$_2$; —C(O)N(OR$^\alpha$)R$^\alpha$; —C(O)C(O)R$^\alpha$; —C(O)CH$_2$C(O)R$^\alpha$; —C(NOR$^\alpha$)R$^\alpha$; —(CH$_2$)$_{0-4}$SSR$^\alpha$; —(CH$_2$)$_{0-4}$S(O)$_2$R$^\alpha$; —(CH$_2$)$_{0-4}$S(O)$_2$OR$^\alpha$; —(CH$_2$)$_{0-4}$OS(O)$_2$R$^\alpha$; —S(O)$_2$NR$^\alpha$$_2$; —(CH$_2$)$_{0-4}$S(O)R$^\alpha$; —N(R$^\alpha$)S(O)$_2$NR$^\alpha$$_2$; —N(R$^\alpha$)S(O)$_2$R$^\alpha$; —N(OR$^\alpha$)R$^\alpha$; —C(NH)NR$^\alpha$$_2$; —P(O)$_2$R$^\alpha$; —P(O)R$^\alpha$$_2$; —OP(O)R$^\alpha$$_2$; —OP(O)(OR$^\alpha$)$_2$; SiR$^\alpha$$_3$; —(C$_{1-4}$ straight or branched)alkylene)O—N(R$^\alpha$)$_2$; or —(C$_{1-4}$ straight or branched)alkylene)-C(O)O—N(R$^\alpha$)$_2$, wherein each R$^\alpha$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aromatic ring having 0-4 heteroatoms independently selected from nitrogen, oxygen, and sulfur, or, notwithstanding the definition above, two independent occurrences of R$^\alpha$, taken together with their intervening atom(s), form a 3-12-membered saturated, partially unsaturated, or aromatic mono- or bi-cyclic ring having 0-4 heteroatoms independently selected from nitrogen, oxygen, and sulfur, which may be substituted as defined below.

Suitable monovalent substituents on R$^\alpha$ (or the ring formed by taking two independent occurrences of R$^\alpha$ together with their intervening atoms), are independently halogen, —(CH$_2$)$_{0-2}$R$^\beta$; -(haloR$^\beta$); —(CH$_2$)$_{0-2}$OH; —(CH$_2$)$_{0-2}$OR$^\beta$; —(CH$_2$)$_{0-2}$CH(OR$^\beta$)$_2$; —O(haloR$^\beta$); —CN; —N$_3$; —(CH$_2$)$_{0-2}$C(O)R$^\beta$; —(CH$_2$)$_{0-2}$C(O)OH; —(CH$_2$)$_{0-2}$C(O)OR$^\beta$; —(CH$_2$)$_{0-2}$SR$^\beta$; —(CH$_2$)$_{0-2}$SH; —(CH$_2$)$_{0-2}$NH$_2$; —(CH$_2$)$_{0-2}$NHR$^\beta$; —(CH$_2$)$_{0-2}$NR$^\beta$$_2$; —NO$_2$; SiR$^\beta$$_3$; —OSiR$^\beta$$_3$; —C(O)SR$^\beta$; —(C$_{1-4}$ straight or branched alkylene)C(O)OR$^\beta$; or —SSR$^\beta$; wherein each RR is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur. Suitable divalent substituents on a saturated carbon atom of R$^\alpha$ include ═O and ═S.

Suitable divalent substituents on a saturated carbon atom of an "optionally substituted" group include the following: ═O; ═S; ═NNR$^\gamma$$_2$; ═NNHC(O)R$^\gamma$; ═NNHC(O)OR$^\gamma$; ═NNHS(O)$_2$R$^\gamma$; ═NR$^\gamma$; ═NOR$^\gamma$; —O(C(R$^\gamma$$_2$))$_{2-3}$O—; or —S(C(R$^\gamma$$_2$))$_{2-3}$S—; wherein each independent occurrence of R$^\gamma$ is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur. Suitable divalent substituents that are bound to vicinal substitutable carbons of an "optionally substituted" group include: —O(CR$^\beta$$_2$)$_{2-3}$O—, wherein each independent occurrence of RR is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur.

Suitable substituents on the aliphatic group of R$^\gamma$ include halogen, —R$^\delta$, -(haloR$^\delta$), —OH, —OR$^\delta$, —O(haloR$^\delta$), —CN, —C(O)OH, —C(O)OR$^\delta$, —NH$_2$, —NHR$^\delta$, —NR$^\delta$$_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

Suitable substituents on a substitutable nitrogen of an "optionally substituted" group include —R$^\varepsilon$, —NR$^\varepsilon_2$, —C(O)R$^\varepsilon$, —C(O)OR$^\varepsilon$, —C(O)C(O)R$^\varepsilon$, —C(O)CH$_2$C(O)R$^\varepsilon$, —S(O)$_2$R$^\varepsilon$, —S(O)$_2$NR$^\varepsilon_2$, —C(S)NR$^\varepsilon_2$, —C(NH)NR$^\varepsilon_2$, or —N(R$^\varepsilon$)S(o)$_2$R$^\varepsilon$; wherein each R$^\varepsilon$ is independently hydrogen, C$_{1-6}$ aliphatic which may be substituted as defined below, unsubstituted —OPh, or an unsubstituted 5-6-membered saturated, partially unsaturated, or aromatic ring having 0-4 heteroatoms independently selected from nitrogen, oxygen, and sulfur, or, notwithstanding the definition above, two independent occurrences of R$^\varepsilon$, taken together with their intervening atom(s) form an unsubstituted 3-12-membered saturated, partially unsaturated, or aromatic mono- or bicyclic ring having 0-4 heteroatoms independently selected from nitrogen, oxygen, and sulfur.

Suitable substituents on the aliphatic group of RE are independently halogen, —R$^\delta$, -(haloR$^\delta$), —OH, —OR$^\delta$, —CN, —C(O)OH, —C(O)OR$^\delta$, —NH$_2$, —NHR$^\delta$, —NR$^\delta_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

The term "substituted" is generally contemplated to include all permissible substituents of organic compounds, "permissible" being in the context of the chemical rules of valence known to those of ordinary skill in the art. In some cases, "substituted" may refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted alkene" must still comprise the alkene carbon-carbon double bond and cannot be modified by substitution, in this definition, to become, e.g., an alkyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be CF$_3$. For purposes of the present disclosure, the heteroatoms such as nitrogen may have hydrogen substituents and/or any permissible substituents of organic compounds described herein which satisfy the valencies of the heteroatoms.

II. Methods for Alkene Homologation

Provided herein are methods for the preparation of C$_6$-C$_{18}$ alkene products. The methods include contacting a C$_4$-C$_{17}$ alkene reactant with a homologation reagent under conditions sufficient to form the C$_6$-C$_{18}$ alkene product. In some embodiments, the alkene reactant is a C$_6$-C$_{17}$ alkene reactant and the alkene product is a C$_8$-C$_{18}$ alkene product. In some embodiments, the C$_6$-C$_{18}$ alkene product comprises a 7-unsaturated alkene, an 8-unsaturated alkene, a 9-unsaturated alkene, or an 11-unsaturated alkene.

A. Alkene Reactants

In some embodiments, the C$_4$-C$_{17}$ alkene reactant is an alkenyl Grignard reagent, an alkenyl sulfonate, or an alkenyl halide. For example, the C$_4$-C$_{17}$ alkene reactant may have a structure according to Formula I:

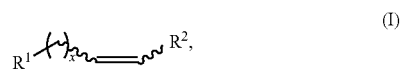

(I)

wherein:
R$^1$ is selected from the group consisting of a Grignard moiety, a sulfonate, or halide;
R$^2$ is selected from the group consisting of hydrogen, C$_1$-C$_{10}$ alkyl, and C$_2$-C$_{10}$ alkenyl; and
subscript x is an integer ranging from 1 to 10.

The alkene reactants can be prepared from commercially available fatty acids and fatty acid esters including, but not limited to, petroselinic acid (6-octadecylenic acid) and methyl dec-9-enoate (9-DAME). Alkene reactants can also be prepared from fatty acid esters such as (Z)-hexadece-11-enoate, which can be obtained via fermentation as described in WO 2017/214133. For example, unsaturated fatty acids and esters thereof may be reduced to the corresponding alkenols using aluminum reagents such as lithium aluminum hydride, sodium bis(2-methoxyethoxy)aluminumhydride (SMEAH; also known by the tradename RED-AL), or diisobutylaluminum hydride (DIBAL; CN 103319704; Chandrasekhar, et al. *Tetrahedron Lett.* 1998, 39, 909).

An alkenol resulting from reduction of a fatty acid or ester thereof may then be converted to a C$_4$-C$_{17}$ alkene reactant of Formula I (e.g., a C$_6$-C$_{17}$ alkene reactant of Formula I) wherein R$^1$ is a sulfonate via reaction with a sulfonyl halide reagent (e.g., a sulfonyl chloride such as p-toluenesulfonyl chloride or methanesulfonyl chloride, or a sulfonyl bromide such as p-toluenesulfonyl bromide or methanesulfonyl bromide) or a sulfonic acid anhydride (e.g., p-toluenesulfonic anhydride, methanesulfonic anhydride). A resulting alkenol may also be converted to a C$_4$-C$_{17}$ alkene reactant of Formula I wherein R is halide via reaction with thionyl halides (e.g., thionyl chloride or thionyl bromide); cyanuric chloride; a tetrahalomethane (e.g., CCl$_4$ or CBr$_4$) in the presence of phosphine (e.g., triphenylphosphine); or an acid such as hydrochloric acid, hydrobromic acid, or the like. The halide reactants can then be converted to C$_4$-C$_{17}$ alkene reactants of Formula I, wherein R$^1$ is a Grignard moiety, by reaction with magnesium metal. In some embodiments, the C$_4$-C$_{17}$ alkene reactant is obtained from hept-6-en-1-ol, oct-7-en-1-ol, (Z)-undec-7-en-1-ol, (Z)-dodec-9-en-1-ol, (Z)-tetradec-9-en-1-ol, dec-9-en-1-ol, methyl dec-9-enoate, undec-10-en-1-ol, or (Z)-hexadec-11-en-1-ol. The alkenols may be obtained, in turn, from unsaturated fatty acids, unsaturated fatty acid methyl esters, or other olefinic starting materials using any combination of the metathesis, reduction, halogenation, or Grignard formation reactions described herein. As a non-limiting example, petroselinic acid or an ester thereof may be converted to hept-6-enoic acid or an ester thereof by ethenolysis with a metathesis catalyst, and the hept-6-enoic acid/ester may then be reduced to provide hept-6-en-1-ol. As another non-limiting example, 7-octenyl acetate may be reacted with 1-pentene in the presence of a Z-selective metathesis catalyst to form (Z)-undec-7-en-1-yl acetate, which may then be hydrolyzed to provide (Z)-undec-7-en-1-ol.

B. Homologation Reagents

In some embodiments, the homologation reagent is a 1,3-diester, an epoxide, a cyanoacetate, a cyanide salt, an orthoester, a haloacetal, a haloalkyl ether, formaldehyde, or a formaldehyde precursor. The homologation reagent will be selected, in part, based on its reactive complementarity to the particular C$_4$-C$_{17}$ alkene reactant employed in the homologation reaction. As non-limiting examples, epoxides and haloacetals are reactive toward alkene reactants having Grignard moieties, while cyanoacetates are reactive toward alkene reactants having leaving groups such as sulfonate groups and halide groups. Other combinations of homologation reagents and alkene reactants, including those described below, can be employed in the homologation step of the methods.

C. Diester Homologation

In some embodiments, the $C_4$-$C_{17}$ alkene reactant is an alkenyl halide or an alkenyl sulfonate, the homologation reagent is a 1,3-diester, and the $C_6$-$C_{18}$ alkene product is a 2-(alkenyl)malonate. The $C_4$-$C_{17}$ alkene reactant may be, for example, a compound according to Formula I wherein $R^1$ is a sulfonate or halide; the homologation reagent may be a 1,3-diester according to Formula (II):

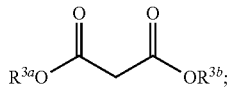
(II)

and the $C_6$-$C_{18}$ alkene product may be a 2-(alkenyl)malonate according to Formula IIIa:

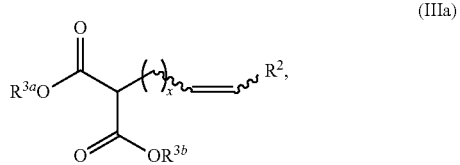
(IIIa)

wherein $R^{3a}$ and $R^{3b}$ are independently selected $C_{1-6}$ alkyl groups. $R^{3a}$ and $R^{3b}$ may independently be, for example, methyl, ethyl, n-propyl, isopropyl, n-butyl, isobutyl, sec-butyl, tert-butyl, n-pentyl, branched pentyl, n-hexyl, or branched hexyl. In some embodiments, $R^{3a}$ and $R^{3b}$ are each methyl.

Scheme 1 shows the synthesis of Z11-unsaturated pheromones through two-carbon homologation according to a non-limiting embodiment of the disclosure.

Scheme 1
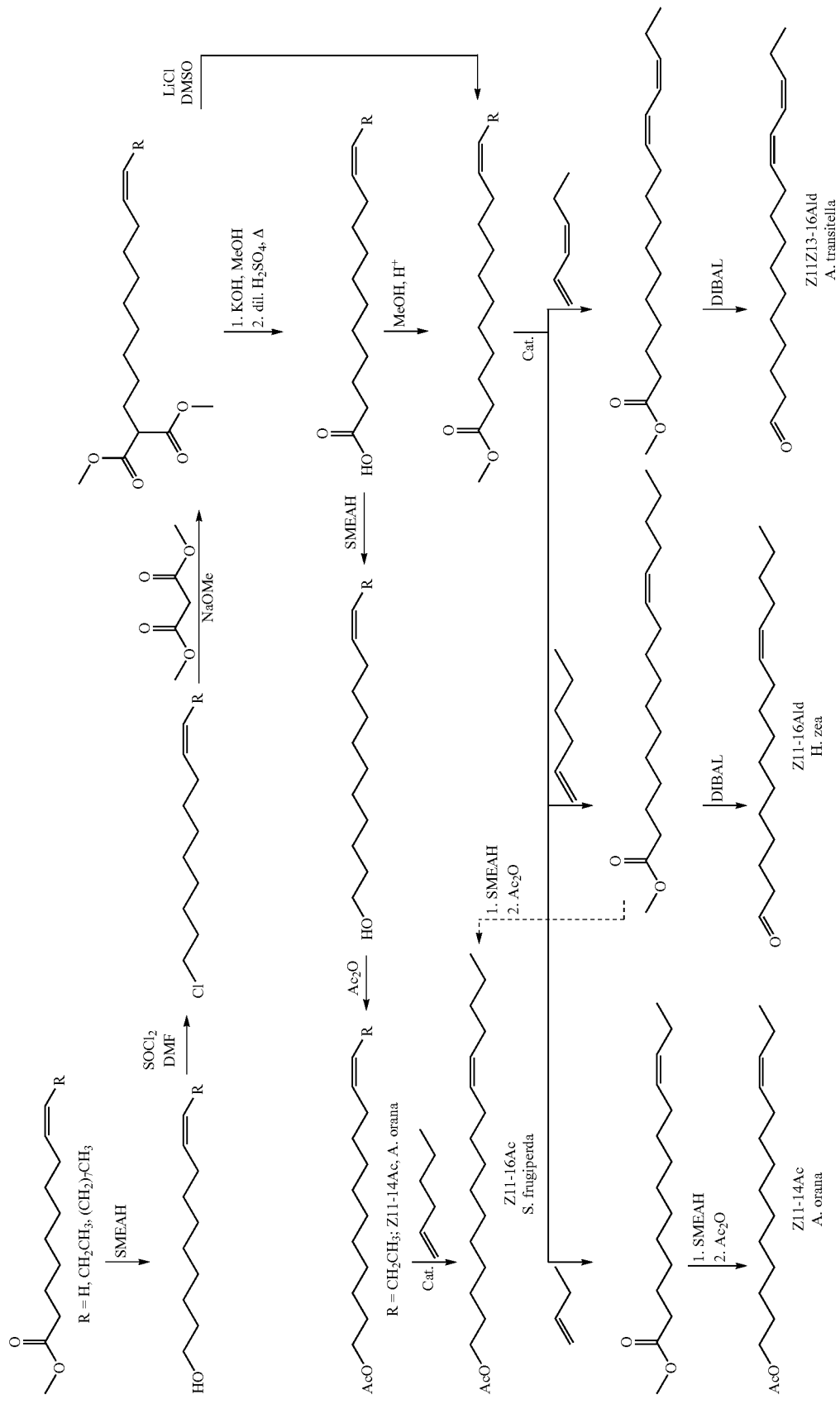

Typically, 0.5-3.5 molar equivalents of the 1,3-diester homologation reagent with respect to the $C_4$-$C_{17}$ alkene reactant will be used. For example, 0.8-2.0 molar equivalents of the 1,3-diester homologation reagent or 0.9-1.1 molar equivalents of the 1,3-diester homologation reagent can be used. In some embodiments, around 0.8, 0.9, 1.0, 1.1, 1.2, 1.3, 1.4, or 1.5 molar equivalents of the 1,3-diester homologation reagent (e.g., dimethyl malonate) with respect to the $C_4$-$C_{17}$ alkene reactant (e.g., an alkenyl chloride or an alkenyl mesylate) is used to form the 2-(alkenyl)malonate. A base can be used to promote displacement of the sulfonate or halide by the 1,3-diester homologation reagent. Examples of suitable bases include sodium methoxide, sodium ethoxide, or potassium tert-butoxide, sodium hydroxide, and sodium carbonate. Typically, 0.1-4 molar equivalents of base with respect to the $C_4$-$C_{17}$ alkene reactant will be employed in the methods provided herein. For example, 0.5-2.5 molar equivalents or 1.75-2.25 molar equivalents of the base can be used. In some embodiments, around 2 molar equivalents of the base (e.g., sodium methoxide) with respect to the $C_4$-$C_{17}$ alkene reactant is used in conjunction with the 1,3-diester homologation reagent (e.g., dimethyl malonate) to form a 2-(alkenyl)malonate according to Formula IIIa. The homologation reaction is typically conducted at temperatures ranging from around −10° C. to about 80° C. for a period of time sufficient to form the homologation product (e.g., from about 1 hour to about 18 hours), depending on the particular 1,3-diester homologation reagent and $C_4$-$C_{17}$ alkene reactant used in the reaction.

The 2-(alkenyl)malonate can be hydrolyzed and decarboxylated, as shown in Scheme 1, to form an alkenoic acid, which can then be esterified to provide the corresponding alkyl alkenoate. In some embodiments, the methods of the present disclosure include converting the 2-(alkenyl)malonate, e.g., a compound according to Formula IIIa, to an alkenoic acid, e.g., a compound according to Formula IIIb:

(IIIb)

esterifying the alkenoic acid to form an alkyl alkenoate, e.g., a compound according to Formula IIIc:

(IIIc)

wherein $R^{3c}$ is $C_{1-6}$ alkyl. $R^{3c}$ may be, for example, methyl, ethyl, n-propyl, isopropyl, n-butyl, isobutyl, sec-butyl, tert-butyl, n-pentyl, branched pentyl, n-hexyl, or branched hexyl. In some embodiments, $R^{3c}$ is methyl.

Metathesis

In some embodiments, the method further includes contacting the alkyl alkenoate, e.g., a compound according to Formula IIIc, with a $C_2$-$C_{10}$ alkene in the presence of a metathesis catalyst under conditions sufficient to form an alkyl alkenoate metathesis product. In some embodiments, the $C_2$-$C_{10}$ alkene is a compound according to Formula IV:

(IV)

and the alkyl alkenoate metathesis product is a compound according to Formula V:

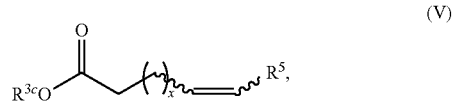
(V)

wherein $R^4$ and $R^5$ are independently selected from the group consisting of hydrogen, $C_{1-8}$ alkyl, and $C_{2-8}$ alkenyl. For example, $R^4$ and $R^5$ may independently be hydrogen, methyl, ethyl, propyl, butyl, pentyl, hexyl, heptyl, octyl, ethenyl, propenyl, butenyl, pentenyl, hexenyl, heptenyl, or octenyl. In some embodiments, $R^4$ is hydrogen and $R^5$ is ethyl, propyl, pentyl, hexyl, heptyl, or octyl. In some embodiments, $R^4$ is hydrogen and $R^5$ is pentenyl, hexenyl, heptenyl, octenyl, or nonenyl. In some embodiments, the $C_2$-$C_{10}$ alkene is propene, but-1-ene, pent-1-ene, hex-1-ene, or (Z)-hexa-1,3-diene.

The metathesis catalysts employed in the methods of the present disclosure generally include at least one metal selected from one of Groups 3-12 of the periodic table or from the lanthanide series. In some embodiments, the metal is selected from Groups 3-8, or, in some cases, from Groups 4-7. In some embodiments, the metal is selected from Group 6. The term "Group 6" refers to the transition metal group comprising chromium, molybdenum, and tungsten. Additionally, the catalysts may be heterogeneous catalysts containing forms of these elements (e.g., by immobilizing a metal complex on an insoluble substrate, for example, silica). Suitable catalysts are described, for example, in WO 2017/087710 and WO 2018/150379, which are incorporated herein by reference in their entirety.

The metathesis reactions employed in the methods can be assessed in terms of the selectivity of the metathesis reaction—that is, the extent to which the reaction produces a particular olefin isomer, whether a Z olefin (i.e., a cis olefin) or an E olefin (i.e., a trans olefin). In general, Z-selective metathesis catalysts provide metathesis products wherein greater than 15% of the olefin is a Z olefin. For example, the metathesis product can contain the Z olefin in an amount ranging from about 20% to about 100% (e.g., from about 25% to about 95%, or from about 30% to about 90%, or from about 35% to about 85%, or from about 40% to about 80%, or from about 45% to about 75%, or from about 50% to about 70%, or from about 55% to about 65%). Depending on the reactants in a particular metathesis reaction, a Z-selective metathesis catalyst may provide products wherein greater than 20%, 25%, 30%, 35%, 40%, 45%, 50%, 55%, 60%, 65%, 70%, 75%, 80%, 85%, 90%, 95%, or 99% of the olefin is a Z olefin. Certain metathesis reactions involving diene starting materials will provide diene metathesis products with mixed olefin stereochemistry. If metathesis product (7E,9Z) dodeca-7,9-dien-1-yl acetate is said to contain Z olefin in an amount of about 97%, for example, it will be understood that the percentage refers to the olefinic bond formed between C9 and C10 of the dodecadiene moiety. The same product may also contain a specified amount of E olefin (e.g., 85%), where the percentage refers to the olefinic bond between C7 and C8 of the dodecadiene moiety.

In certain instances, Z-selectivity is afforded by catalysts containing a Group 6 metal, such as tungsten or molybdenum, bonded to a large, freely rotating aryloxide (e.g., substituted or unsubstituted [1,1'-binaphthalen]-2-ol, substituted or unsubstituted octahydro-[1,1'-binaphthalen]-2-ol, or the like) as well as a smaller imido substituent (e.g., a substituted or unsubstituted phenyl imido group, a substituted or unsubstituted adamantylimido group, or the like). It is believed that a catalyst of this type can provide a Z olefin product via formation of a syn alkylidene adduct and an all-cis metallocyclobutane intermediate. In other instances, Z-selectivity is afforded by catalysts containing a Group 8 metal, such as ruthenium or osmium, bonded to a chelating group (e.g., an adamantly group) bearing an N-heterocyclic carbene ligand (e.g., a substituted or unsubstituted dihydroimidazole). In such cases, a Z olefin product can result from attack of a metal-alkylidene complex by an olefin via a pathway to form a syn-metallocycle with substituents pointing away from the N-heterocyclic carbene ligand.

In general, E-selective catalysts provide metathesis products wherein greater than 50% of the olefin is an E olefin. Preferably, E-selective catalysts provide metathesis products wherein greater than 85% of the olefin is an E olefin. For example, the metathesis product can contain the E olefin in an amount ranging from about 86% to about 100%. The metathesis product can contain the E olefin in an amount ranging from about 86% to about 99%, or from about 88% to about 98%, or from about 90% to about 96%, or from about 92% to about 94%. The metathesis product can contain the E olefin in an amount ranging from about 86% to about 89%, or from about 89% to about 92%, or from about 92% to about 95%, or from about 95% to about 98%. The metathesis product can contain the E olefin in an amount of about 86%, 87%, 88%, 89%, 90%, 91%, 92%, 93%, 94%, 95%, 96%, 97%, 98%, 99%, or 100%. Formation of E olefin products will be favored in many cases due to the greater thermodynamic stability of the E olefin as compared to the corresponding Z olefin.

In some embodiments, the metathesis catalyst has a structure according to Formula L:

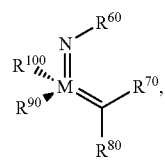

(L)

wherein:

M is Mo or W;

$R^{60}$ is selected from optionally substituted aryl, optionally substituted heteroaryl, optionally substituted aliphatic, and optionally substituted heteroaliphatic;

each of $R^{70}$ and $R^{80}$ is independently selected from hydrogen, optionally substituted aliphatic, optionally substituted heteroaliphatic, optionally substituted aryl, and optionally substituted heteroaryl;

$R^{90}$ is selected from —O-alkyl, —O-heteroalkyl, —O-aryl, —O-heteroaryl, —N(R″)-alkyl, —N(R″)-heteroalkyl, —N(R″)-aryl, and —N(R″)-heteroaryl, wherein each R″ is independently selected from hydrogen, an amino protecting group, and optionally substituted alkyl, and wherein $R^{90}$ is optionally substituted; and $R^{100}$ is selected from aryl, heteroaryl, alkyl, heteroalkyl, cycloalkyl, heterocycloalkyl, —O-alkyl, —O-heteroalkyl, —O-aryl, and —O-heteroaryl, each of which is optionally substituted, or $R^{100}$ is halogen.

In some embodiments, the metathesis catalyst has a structure according to Formula L and the metathesis product comprises a Z olefin.

In some embodiments, $R^{90}$ is an optionally substituted asymmetric —O-aryl group and $R^{100}$ is an optionally substituted heteroaryl group.

In some cases, the metal complex includes one or more oxygen-containing ligands lacking a plane of symmetry or nitrogen-containing ligands lacking a plane of symmetry (i.e., asymmetric ligands). In some embodiments, such ligands can coordinate the metal atom via an oxygen atom (e.g., via a hydroxyl group) or other atom of the ligand. The oxygen-containing ligand can coordinate the metal atom via one site of the ligand, i.e., the ligand may be a monodentate ligand.

In some embodiments, a ligand can comprise two sites capable of binding the metal center, wherein a first site is bonded to a protecting group, or other group, that may reduce the ability of the first site to coordinate the metal, and the second site coordinates the metal center. For example, the ligand can be a [1,1'-binaphthalene]-2,2'-diol (BINOL) derivative having two hydroxyl groups, wherein one hydroxyl group is bonded to a protecting group (e.g., a silyl protecting group) and another hydroxyl group coordinates the metal center.

In some embodiments, an asymmetric oxygen-containing ligand is of the following structure:

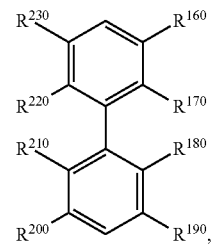

wherein:

$R^{160}$ is an optionally substituted group selected from aryl, heteroaryl, alkyl, or heteroalkyl;

$R^{170}$ is hydrogen, —OH, halogen, —OPG, or an optionally substituted group selected from aliphatic, heteroaliphatic, aryl, aryloxy, heteroaryl, heteroaryloxy, acyl, and acyloxy;

or, together $R^{160}$ and $R^{170}$ are joined to form an optionally substituted partially unsaturated or aryl ring;

$R^{180}$ is —OH, —OPG, or an optionally substituted amino group;

$R^{190}$ is hydrogen, halogen, an optionally substituted group selected from aliphatic, heteroaliphatic, aryl, heteroaryl, or acyl;

each of $R^{200}$, $R^{210}$, $R^{220}$, and $R^{230}$ is independently aryl, heteroaryl, aliphatic, heteroaliphatic, or acyl, optionally substituted;

or, together $R^{200}$ and $R^{210}$ are joined to form an optionally substituted partially unsaturated or aryl ring;

or, together $R^{220}$ and $R^{230}$ are joined to form an optionally substituted partially unsaturated or aryl ring; and each PG is independently a hydroxyl protecting group.

In some embodiments, $R^{60}$ is selected from

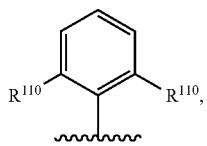 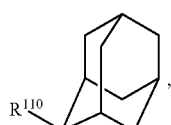

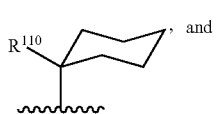, and 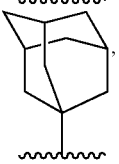

wherein each $R^{110}$ is independently hydrogen or a monovalent substituent.

In some embodiments, $R^{100}$ is an optionally substituted group selected from

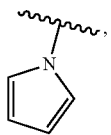, 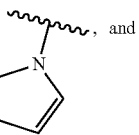, and

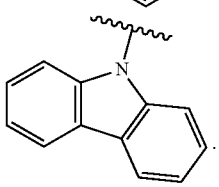.

In some embodiments, $R^{90}$ is an optionally substituted group selected from:

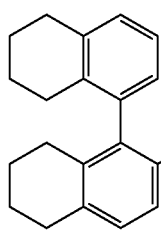 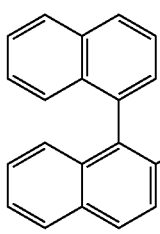

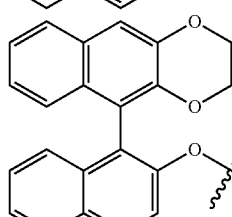 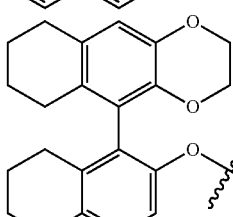

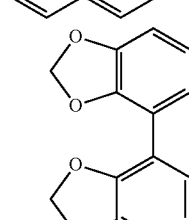 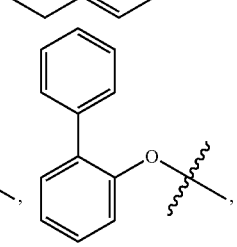

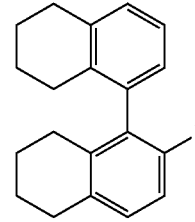 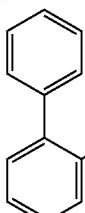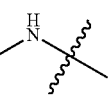

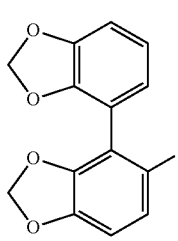 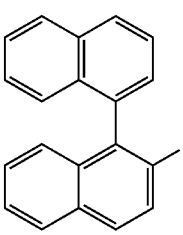

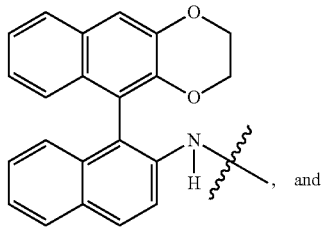, and

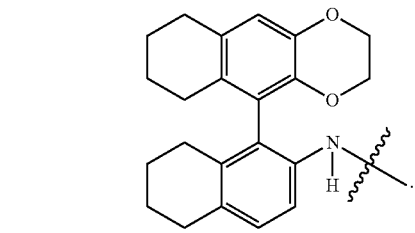.

In some embodiments, $R^{90}$ is

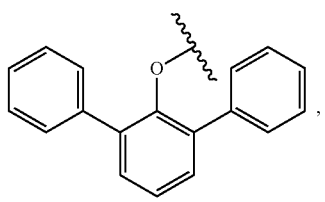 [SMILES: *Oc1c(-c2ccccc2)cccc1-c1ccccc1], which is optionally substituted.

In some embodiments, the metathesis catalyst is selected from

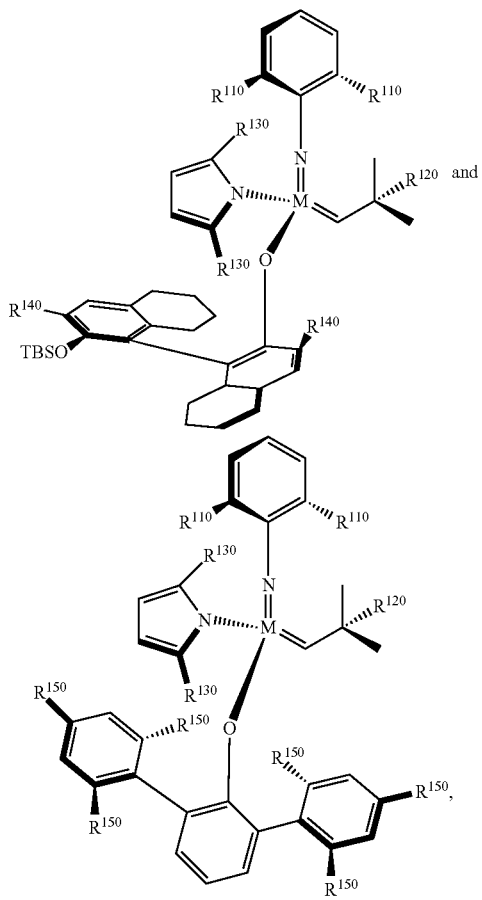

wherein M is Mo or W;
each $R^{110}$ is independently selected from halo and alkyl;
$R^{120}$ is selected from the group of consisting of alkyl, aryl, alkenyl, and heteroaryl;
each $R^{130}$ is independently selected from hydrogen, halo, alkyl, aryl, and heteroaryl;
each $R^{140}$ is independently selected from halo, alkyl, aryl, and heteroaryl; and
each $R^{150}$ is independently an optionally substituted alkyl.

In some embodiments, the metathesis catalyst has a structure according to Formula LI:

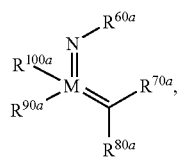

(LI)

wherein:
M is Mo or W;
$R^{60a}$ is selected from optionally substituted aryl, optionally substituted heteroaryl, optionally substituted alkyl, optionally substituted heteroalkyl, optionally substituted cycloalkyl, and optionally substituted heterocycloalkyl, and
$R^{70a}$ and $R^{80a}$ are independently selected from hydrogen, optionally substituted alkyl, optionally substituted alkenyl, optionally substituted heteroalkyl, optionally substituted heteroalkenyl, optionally substituted aryl, and optionally substituted heteroaryl;
$R^{100a}$ is selected from optionally substituted alkyl, optionally substituted alkoxy, optionally substituted heteroalkyl, optionally substituted aryl, optionally substituted aryloxy, optionally substituted heteroaryl, optionally substituted silylalkyl, and optionally substituted silyloxy; and
$R^{90a}$ is $R^{110a}$—X—, wherein
X is O or S and $R^{110a}$ is optionally substituted aryl; or
X is O and $R^{110a}$ is $SiR^{120a}R^{130a}R^{140a}$ or $CR^{150a}R^{160a}R^{170a}$, wherein $R^{120a}$, $R^{130a}$, $R^{140a}$, $R^{150a}$, $R^{160a}$, and $R^{170a}$ are independently selected from optionally substituted alkyl and optionally substituted phenyl; or
$R^{90a}$ and $R^{100a}$ are linked together and are bonded to M via oxygen.

In some embodiments, the metathesis catalyst has a structure according to Formula LI and the metathesis product comprises a Z olefin.

In some embodiments, the catalyst is a compound of Formula LI wherein:
$R^{100a}$ is selected from the group consisting of alkyl, alkoxy, heteroalkyl, aryl, aryloxy, and heteroaryl, each of which is optionally substituted; and
X is O or S and $R^{110a}$ is optionally substituted aryl; or
X is O and $R^{110a}$ is $CR^{150a}R^{160a}R^{170a}$.

In some embodiments, the catalyst is a compound of Formula LI wherein:
$R^{60a}$ is selected from the group consisting of 2,6-dimethylphenyl; 2,6-diisopropylphenyl; 2,6-dichlorophenyl; and adamant-1-yl;
$R^{70a}$ is selected from the group consisting of —C(CH$_3$)$_2$C$_6$H$_5$ and —C(CH$_3$)$_3$;
$R^{80a}$ is H;
$R^{100a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and
$R^{90a}$ is $R^{110a}$—X—, wherein
X═O and
$R^{110a}$ is phenyl which bears two substituents in the ortho positions with respect to O, or which bears at least three substituents, from which two substituents are in the ortho positions with respect to O and one substituent is in the para position with respect to O; or
$R^{110a}$ is selected from the group consisting of optionally substituted 8-(naphthalene-1-yl)-naphthalene-1-yl; optionally substituted 8-phenylnaphthalene-1-yl; optionally substituted quinoline-8-yl; triphenylsilyl; triisopropylsilyl; triphenylmethyl; tri(4-methylphenyl)methyl; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

In some embodiments, the catalyst is a compound of Formula LI wherein:
$R^{100a}$ is selected from the group consisting of pyrrol-1-yl; 2,5-dimethyl-pyrrol-1-yl; and
$R^{110a}$ is phenyl which bears two substituents in the ortho positions with respect to O, or which bears at least three substituents, from which two substituents are in the ortho positions with respect to O and one substituent is in the para position with respect to O; or $R^{110a}$ is selected from the group consisting of optionally substituted 8-(naphthalene-1-yl)-naphthalene-1-yl and optionally substituted 8-phenylnaphthalene-1-yl.

In some embodiments, the catalyst is a compound of Formula LI wherein $R^{70}$ is selected from 4-bromo-2,6-diphenylphenoxy; 4-fluoro-2,6-diphenylphenoxy; 4-methyl-2,6-diphenylphenoxy; 4-methoxy-2,6-diphenylphenoxy; 4-dimethylamino-2,6-diphenylphenoxy; 2,4,6-triphenylphenoxy; 4-fluoro-2,6-dimesitylphenoxy; 4-bromo-2,6-di-tert-butylphenoxy; 4-methoxy-2,6-di-tert-butylphenoxy; 4-methyl-2,6-di-tert-butylphenoxy; 2,4,6-tri-tert-butylphenoxy; 4-bromo-2, 3,5,6-tetraphenylphenoxy; 4-bromo-2,6-di(4-bromophenyl)-3,5-diphenylphenoxy; 2,6-diphenylphenoxy; 2,3,5,6-tetraphenylphenoxy; 2,6-di(tert-butyl)phenoxy; 2,6-di(2,4,6-triisopropylphenyl)phenoxy; triphenylsilyloxy; triisopropylsilyloxy; triphenylmethyloxy; tri(4-methyphenyl)methyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy;

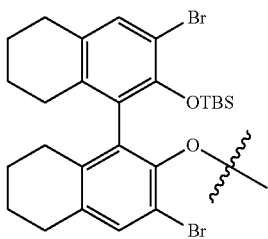 [SMILES: *Oc1c(Br)cc2c(c1-c1c3c(cc(Br)c1O[Si](C)(C)C(C)(C)C)CCCC3)CCCC2]

wherein TBS is t-butyldimethylsilyl; or

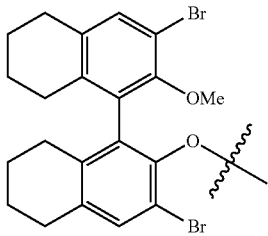

wherein Me=methyl.

In some embodiments, the metathesis catalyst has a structure according to Formula LII.

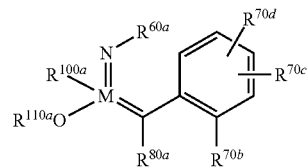

(LII)

$R^{60a}$ is aryl, heteroaryl, alkyl, or cycloalkyl, each of which is optionally substituted;
$R^{100a}$ is pyrrolyl, imidazolyl, indolyl, pyrazolyl, azaindolyl, or indazolyl, each of which is optionally substituted;
$R^{110a}$ is optionally substituted aryl;
$R^{80a}$ is a hydrogen atom, alkyl, or alkoxy;
$R^{70b}$ is a hydrogen atom, —O—($C_{1-6}$ alkyl), —$CH_2$—O—($C_{1-6}$ alkyl), heteroalkoxy, or —N($C_{1-6}$ alkyl)$_2$;
$R^{70c}$ and $R^{70d}$ are independently a hydrogen atom, $C_{1-6}$ alkyl, $C_{1-6}$ alkoxy, a halogen atom, —$NO_2$, an amide, or a sulfonamide.

In some embodiments, the metathesis catalyst has a structure according to Formula LII and the metathesis product comprises a Z olefin.

In some embodiments, $R^{60a}$ in the metathesis catalyst according to LII is phenyl, 2,6-dichlorophenyl, 2,6-dimethylphenyl, 2,6-diisopropylphenyl, 2-trifluoromethyl-phenyl, pentafluorophenyl, tert-butyl, or 1-adamantyl.

In some embodiments, $R^{110a}$ is:

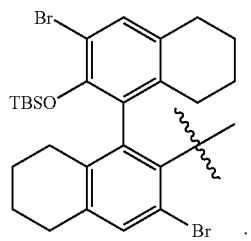 [SMILES: *c1c(Br)cc2c(c1-c1c3c(cc(Br)c1O[Si](C)(C)C(C)(C)C)CCCC3)CCCC2]

In some embodiments, $R^{70b}$ is methoxy, $R^{70c}$ is hydrogen, and $R^{70d}$ is hydrogen.

In some embodiments, the metathesis catalyst is selected from the group consisting of:

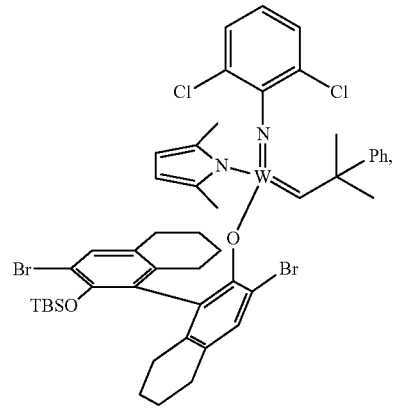

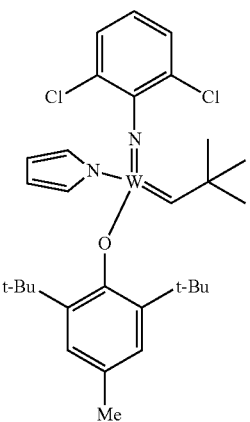

-continued

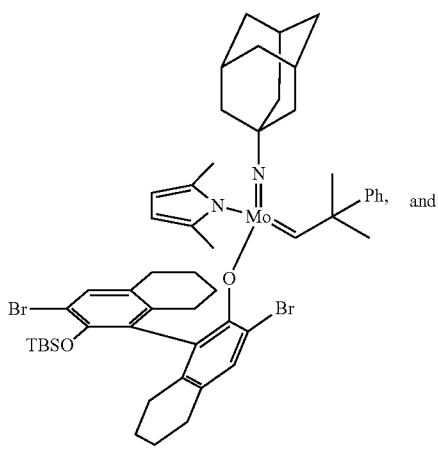

In some embodiments, the metathesis catalyst is:

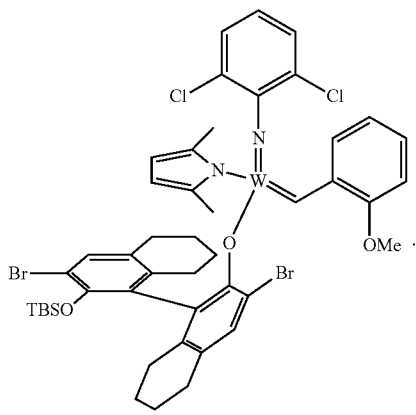

In some embodiments, the metathesis catalyst is:

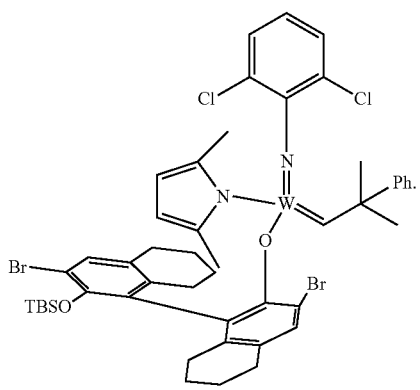

In some embodiments, the metathesis catalyst is:

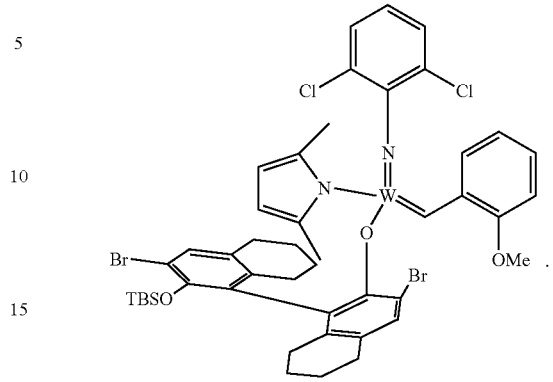

The catalyst is typically provided in the reaction mixture in a sub-stoichiometric amount (e.g., a catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the methods include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr (e.g., less than about 750, 700, 650, 600, 550, 500, 450, 400, 350, 300, 250, 500, 150, 100, 90, 80, 70, 60, 50, 40, 30, 20, 10, 5, or 1 torr).

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of 1:2.

In some embodiments, one molar equivalent of the $C_2$-$C_{10}$ alkene is contacted with one molar equivalent of the alkyl alkenoate. In some embodiments, about 1.5, 2, 2.5, or 3 molar equivalents of the $C_2$-$C_{10}$ alkene is contacted with one molar equivalent of the alkyl alkenoate. In some embodiments, about 1.5 molar equivalents of the olefin is contacted with one molar equivalent of the alkyl alkenoate.

In general, the reactions with many of the metathesis catalysts disclosed herein provide yields better than 15%, e.g., better than 50%, or better than 75%, or better than 90%. In addition, the reactants and products are chosen to provide at least a 5° C. difference, e.g., a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, e.g., less than 12 hours, or less than 8 hours, or less than 4 hours. Advantageously, metathesis products formed in the methods can be prepared on a scale ranging from a few milligrams to hundreds of kilograms or more. For example, the methods can be conducted using around 1-10 grams of the $C_2$-$C_{10}$ alkene; or around 10-100 grams of the $C_2$-$C_{10}$ alkene; or around 100-500 grams of the $C_2$-$C_{10}$ alkene; or around 500-1000 grams of the $C_2$-$C_{10}$ alkene. The methods can be conducted using at least 1, 5, 10, 25, 50, 100, or 1,000 kilograms of starting material. The metathesis reactions can be conducted using a metathesis reactor as described, for example, in WO 2011/046872, which reactor may be operated in conjunction with one or more downstream separation units for separating and/or recycling particular product or byproduct streams (e.g., an olefin stream, a $C_2$-$C_3$ compound stream, or a $C_3$-$C_5$ compound stream). The metathesis reactor and separation unit(s) can be operated in conjunction with one or more adsorbent beds to facilitate the separation of the metathesized products from the catalyst, as well as washing and drying units for purification of desired products. The metathesis, reduction, and acylation reactions can be conducted to provide products on the scale of metric tons.

One of skill in the art will appreciate that the time, temperature and solvent can depend on each other, and that changing one can require changing the others to prepare the metathesis products in the methods. The metathesis steps can proceed at a variety of temperatures and times. In general, metathesis reactions are conducted using reaction times of several minutes to several days. For example, metathesis reaction times of from about 12 hours to about 7 days can be used. In some embodiments, metathesis reaction times of 1-5 days can be used. In some embodiments, metathesis reaction times of from about 10 minutes to about 10 hours can be used. In general, the metathesis reactions are conducted at a temperature of from about 0° C. to about 200° C. For example, a metathesis reaction can be conducted at 15-100° C. In some embodiments, the reaction is conducted at 20-80° C. In some embodiments, the reaction is conducted at 100-150° C.

In certain instances, the efficacy of the metathesis catalyst can be improved (e.g., the turnover number can be increased or the overall catalyst loading may be decreased) through slow addition of the catalyst to a substrate. The overall catalyst loading can be decreased by at least 10%, at least 20%, or at least 30% when administered slowly to achieve the same turnover number as a single, full batch loading. The slow addition of overall catalyst loading can include adding fractional catalyst loadings to the reaction materials at an average rate of approximately 10 ppm by weight of catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In some embodiments, the catalyst is slowly added at a rate of between about 0.01-10 ppmwt/hr, 0.05-5 ppmwt/hr, or 0.1-1 ppmwt/hr. The slow addition of the catalyst can be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

Reduction

In some embodiments, the method further comprises contacting the alkyl alkenoate metathesis product with a reducing agent under conditions sufficient to form an alkenol, e.g., an alkenol according to Formula VI:

(VI)

Any suitable conditions for reducing the alkyl alkenoate metathesis product can be employed. Homogenous or heterogenous conditions can be used. Examples of homogenous conditions include, but are not limited to: hydrogenolysis using ligated precious metal catalysts (Tan, et al. *Org. Lett.* 2015, 17 (3), 454; Spasyuk, D. et al. *J. Am. Chem. Soc.* 2015, 137, 3743; WO 2014/139030), metal hydride-catalyzed reduction using silane reagents (Mimoun, H. *J Org. Chem.* 1999, 64, 2582; U.S. Pat. No. 6,533,960); and reduction using aluminum reagents. Alkenols can also be prepared from alkyl alkenoates via hydrogenolysis with heterogeneous catalysts, such as ZnO or CuO/ZnO supported on chromite, alumina, or other material. Typically, 1-2 molar equivalents of the reducing agent with respect to the alkyl alkenoate metathesis product will be used. In some embodiments, around 1.0, 1.1, 1.2, 1.3, 1.4, or 1.5 molar equivalents of the reducing agent with respect to the alkyl alkenoate metathesis product is used to form the corresponding alkenol.

Any suitable solvent can be used for reducing the alkyl alkenoate metathesis product. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. The reduction reaction is typically conducted at temperatures ranging from around −78° C. to about 25° C. for a period of time sufficient to form the alkenol. The reaction can be conducted for a period of time ranging from a few minutes to several hours or longer, depending on the particular alkyl alkenoate metathesis product and reducing agent used in the reaction. For example, the reduction of methyl (Z)-tetradec-11-enoate with an aluminum reagent (e.g., SMEAH) can be conducted for 1-2 hours at a temperature ranging from around 0° C. to around 20° C.

Esterification

In some embodiments, the method further includes contacting the alkenol with an acylating agent under conditions sufficient to form an alkenol ester, e.g., an alkenol ester according to Formula VII:

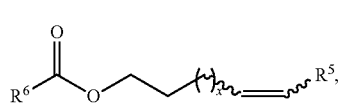
(VII)

wherein $R^6$ is $C_{1-6}$ alkyl. $R^6$ may be, for example, methyl, ethyl, n-propyl, isopropyl, n-butyl, isobutyl, sec-butyl, tert-butyl, n-pentyl, branched pentyl, n-hexyl, or branched hexyl. In some embodiments, the alkenol is an alkenyl acetate wherein $R^6$ is methyl.

Any acylating agent suitable for forming the alkenol ester can be used in the methods. Examples of suitable acylating agents include acid anhydrides (e.g., acetic anhydride), acid chlorides (e.g., acetyl chloride), activated esters (e.g., pentafluorophenyl esters of carboxylic acids), and carboxylic acids used with coupling agents such as dicyclohexylcarbodiimide or carbonyl diimidazole. Typically, 1-10 molar equivalents of the acylating agent with respect to the alkenol will be used. For example, 1-5 molar equivalents of the acylating agent or 1-2 molar equivalents of the acylating agent can be used. In some embodiments, around 1.0, 1.1, 1.2, 1.3, 1.4, or 1.5 molar equivalents of the acylating agent (e.g., acetic anhydride) with respect to the alkenol is used to form the alkenol ester.

A base can be used to promote acylation of the alkenol by the acylating agent. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. Typically, less than one molar equivalent of base with respect to the alkenol will be employed in the methods. For example, 0.05-0.9 molar equivalents or 0.1-0.5 molar equivalents of the base can be used. In some embodiments, around 0.05, 0.1, 0.15, or 0.2 molar equivalents of the base (e.g., sodium acetate) with respect to the alkenol is used in conjunction with the acylating agent (e.g., acetic anhydride) to form the alkenol ester.

Any suitable solvent can be used for acylating the alkenol. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alternatively, an alkenol can be combined with an acylating agent such as acetic anhydride and a base such as sodium acetate without an additional solvent. The acylation reaction is typically conducted at temperatures ranging from around 25° C. to about 100° C. for a period of time sufficient to form the alkenol ester. The reaction can be conducted for a period of time ranging from a few minutes to several hours or longer, depending on the particular alkenol and acylating agent used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C. In some embodiments, the alkenol ester is an alkenyl acetate. In some embodiments, the alkenyl acetate is an insect pheromone.

Partial Reduction

Alkyl alkenoate metathesis products, e.g., a metathesis product according to Formula V, can be partially reduced to form the corresponding alkenal, e.g., an alkenal according to Formula VIII:

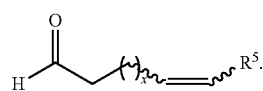
(VIII)

The partial reduction can be carried out with a reagent such as amine-modified sodium SMEAH or DIBAL. The amine-modified SMEAH can be generated in situ via reaction of the SMEAH with either a primary amine or secondary amine (as described, for example, by Shin, et al. *Bull. Korean Chem. Soc.* 2014, 35, 2169, which is incorporated herein by reference). Accordingly, some embodiments of the present disclosure provide methods which further include contacting the alkyl alkenoate metathesis product with a reducing agent under conditions sufficient to form an alkenal (i.e., an alkenyl aldehyde).

Reduction steps, acylation steps, and metathesis steps such as those described above can be conducted in various combinations and sequences. In some embodiments, for example, the methods provided herein includes reducing an alkenoic acid, e.g., an acid according to Formula IIIb, to form an alkenol, e.g., an alkenol according to Formula IIId:

(IIId)

The alkenoic acid can be reduced with SMEAH or another reducing agent as described above, and the resulting alkenol can be acylated to form an alkenol ester, e.g., an alkenol ester according to Formula IX:

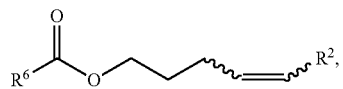
(IX)

wherein $R^6$ is as described above. A metathesis catalyst can then be used in the reaction of an alkenol ester according to Formula IX with a $C_2$-$C_{10}$ alkene according to Formula IV, providing a metathesis product according to Formula VII. In some embodiments, the alkenol ester is an alkenyl acetate, and the metathesis product is an insect pheromone.

D. Cyanide/Cyanoacetate Homologation

In some embodiments, the $C_4$-$C_{17}$ alkene reactant is an alkenyl halide or an alkenyl sulfonate, the homologation reagent is a cyanoacetate and the $C_6$-$C_{18}$ alkene product is an alkyl (2-cyano)alkenoate. The $C_4$-$C_{17}$ alkene reactant may be, for example, a compound according to Formula I wherein $R^1$ is a sulfonate or halide; the homologation reagent may be a cyanoacetate having the formula (NC)CH$_2$COOR$^{3d}$; and the C$_6$-C$_{18}$ alkene product may be an alkyl (2-cyano)alkenoate according to Formula X:

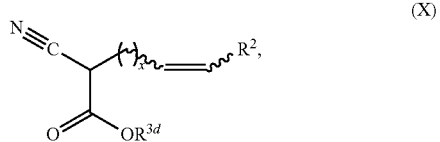

(X)

wherein $R^{3d}$ is C$_{1-6}$ alkyl. $R^{3d}$ may be, for example, methyl, ethyl, n-propyl, isopropyl, n-butyl, isobutyl, sec-butyl, tert-butyl, n-pentyl, branched pentyl, n-hexyl, or branched hexyl. In some embodiments, $R^{3d}$ is ethyl.

Scheme 2 shows the synthesis of (Z)-octadec-13-enal (Z13-18Ald), a pheromone produced by the Asiatic rice borer (*Chilo suppressalis*) according to a non-limiting embodiment of the disclosure. Fermentation-derived methyl (Z)-hexadec-11-enoate (Z11-16 FAME) can be reduced with sodium bis(2-methoxyethoxy)-aluminum hydride (SMEAH) or another reducing agent to produce the corresponding alcohol, which can be extended by two-carbon homologation with ethyl cyanoacetate prior to decarboxylation and DIBAL reduction.

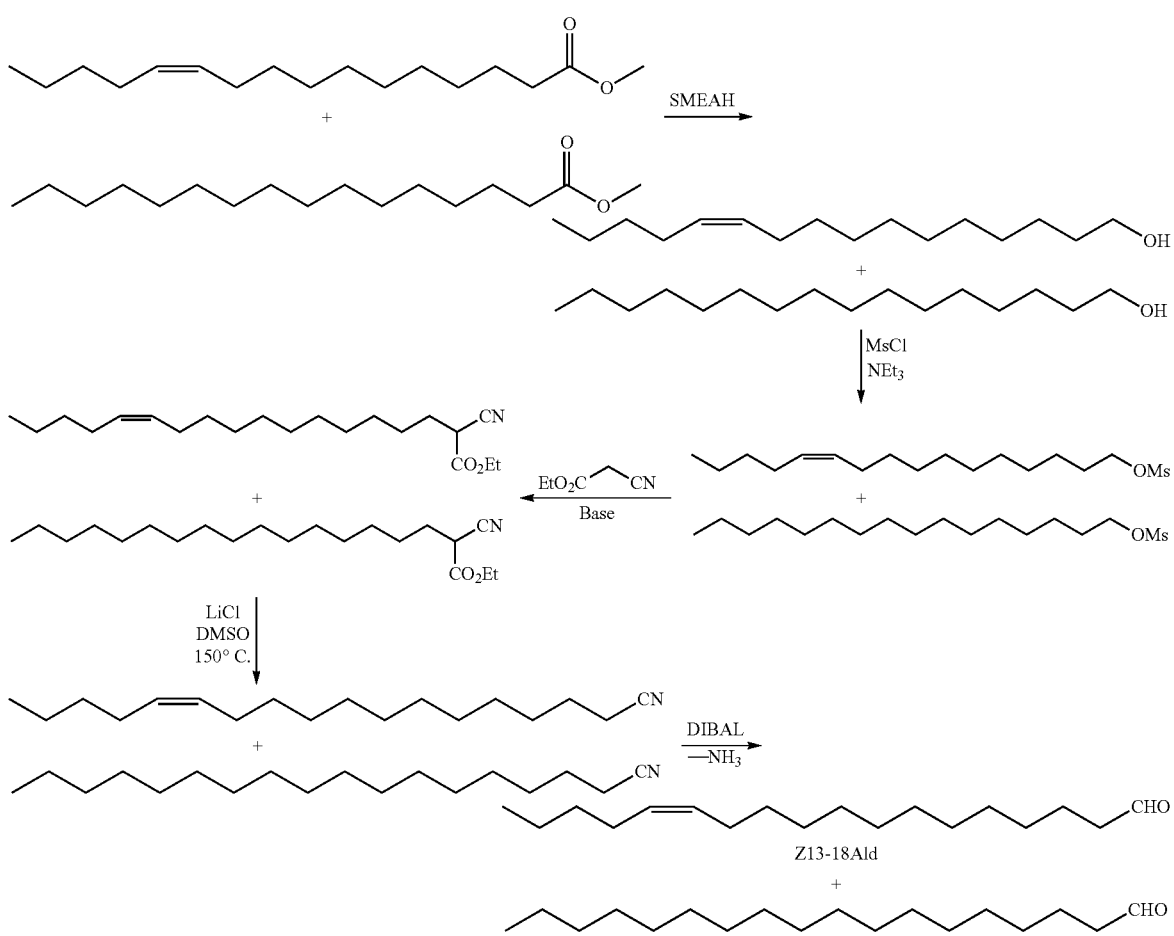

Scheme 3 shows the synthesis of (Z)-hexadec-11-enal (Z11-16Ald; an *H. zea* pheromone), (Z)-hexadec-11-en-1-yl acetate (Z11-16Ac; an *S. frugiperda* pheromone), and (Z)-tetradec-11-en-1-yl acetate (Z11-14Ac; an *A. orana* pheromone) from metathesis-derived (Z)-dodec-9-en-1-ol (Z9-12OH) and (Z)-tetradec-9-en-1-ol (Z9-14OH) via two-carbon homologation with ethyl cyanoacetate, followed by decarboxylation and DIBAL reduction according to an embodiment of the disclosure.

Scheme 3
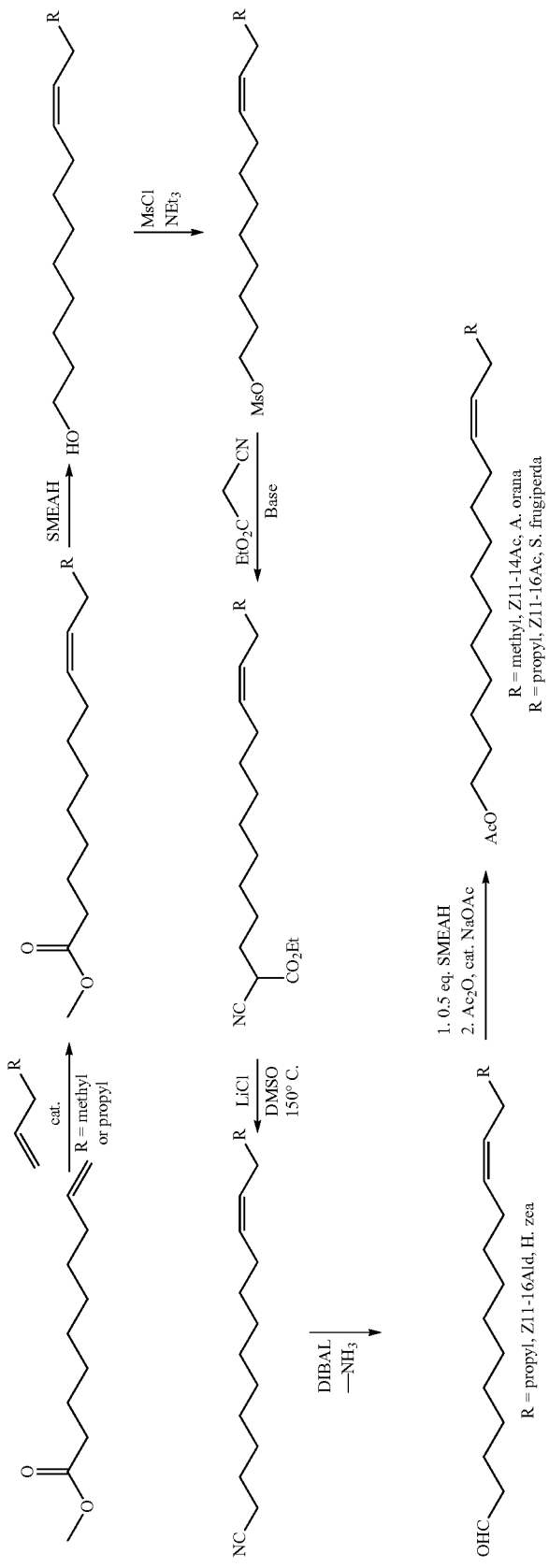

Scheme 4 shows the synthesis of Z11-16Ald, Z11-16Ac and Z11-14Ac from methyl dec-9-enoate (9-DAME) via two-carbon homologation with ethyl cyanoacetate, decarboxylation and DIBAL reduction according to a non-limiting embodiment of the disclosure.

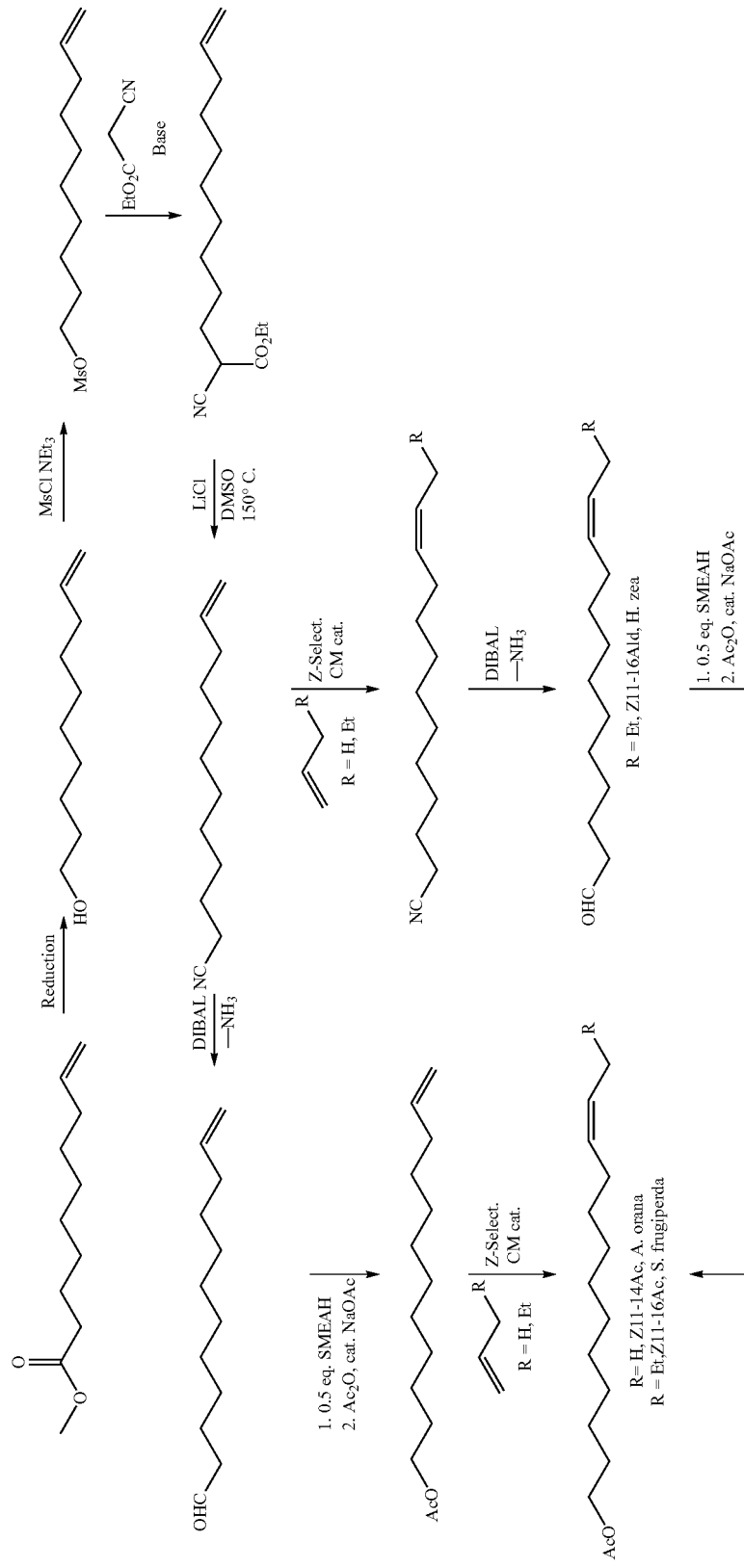
Scheme 4

Typically, 0.5-4.0 molar equivalents of the cyanoacetate homologation reagent with respect to the $C_4$-$C_{17}$alkene reactant will be used. For example, 0.75-3.5 molar equivalents of the cyanoacetate homologation reagent or 1.5-3.25 molar equivalents of the cyanoacetate homologation reagent can be used. In some embodiments, around 2.8, 2.9, 3.0, 3.1, or 3.2 molar equivalents of the cyanoacetate homologation reagent (e.g., ethyl cyanoacetate) with respect to the $C_4$-$C_{17}$alkene reactant (e.g., an alkenyl mesylate or an alkenyl chloride) is used to form the alkyl (2-cyano)alkenoate. A base can be used to promote displacement of the sulfonate or halide by the cyanoacetate homologation reagent. Examples of suitable bases include sodium hydride, sodium methoxide, sodium ethoxide, or potassium tert-butoxide, sodium hydroxide, and sodium carbonate. Typically, 0.1-4 molar equivalents of base with respect to the $C_4$-$C_{17}$alkene reactant will be employed in the methods. For example, 0.5-2 molar equivalents or 1-1.75 molar equivalents of the base can be used. In some embodiments, around 1.5 molar equivalents of the base (e.g., sodium hydride) with respect to the $C_4$-$C_{17}$alkene reactant is used in conjunction with the cyanoacetate homologation reagent (e.g., ethyl cyanoacetate) to form an alkyl (2-cyano)alkenoate according to Formula IIa. The homologation reaction is typically conducted at temperatures ranging from around $-10°$ C. to about $80°$ C. for a period of time sufficient to form the homologation product (e.g., from about 1 hour to about 18 hours), depending on the particular cyanoacetate homologation reagent and $C_4$-$C_{17}$ alkene reactant used in the reaction.

In some embodiments, the method further includes decarboxylating the alkyl (2-cyano)alkenoate to form an alkenyl nitrile, e.g., a nitrile according to Formula XI:

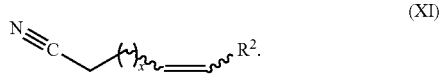

(XI)

Decarboxylation can be promoted by heating the alkyl (2-cyano)alkenoate at temperature ranging from about $50°$ C. to about $200°$ C., optionally in the presence of lithium chloride, sodium chloride, or a like halide. The decarboxylation can be conducted in a solvent such as dimethyl sulfoxide, dimethylformamide, or the like.

In some embodiments, the method further includes reducing the alkenyl nitrile to form an alkenal, e.g., an alkenal according to Formula XII:

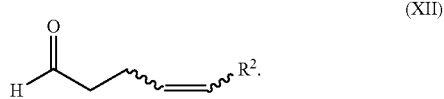

(XII)

Reduction of nitriles with diisobutylaluminum hydride (DIBAL), for example, results in the formation of aldehydes due to formation of a Lewis acid-base complex between the nitrile and aluminum center prior to hydride transfer. Alkenals can be further reduced to form the corresponding alkenols, which can be further acylated to form the corresponding alkenol esters (e.g., alkenyl acetates). Metathesis steps as described above, can be performed before or after such steps. In some embodiments, the alkenal(s), alkenol(s), and/or alkenyl acetate(s) prepared in this manner are insect pheromone(s).

Nitriles according to Formula XI can also be prepared from alkene reactants using cyanide salts. In some embodiments, the $C_4$-$C_{17}$ alkene reactant is an alkenyl sulfonate or an alkenyl halide, the homologation reagent is a cyanide salt (e.g., sodium cyanide), and the $C_6$-$C_{18}$ alkene product is an alkenyl nitrile. Alternatively, alkenols can be converted to nitriles directly using sodium cyanide (e.g., 1.5-2.5 molar equivalents), chlorotrimethylsilane or iodotrimethylsilane (e.g., 1.5-2.5 molar equivalents), and catalytic sodium iodide as depicted in Scheme 5.

Scheme 5 shows the synthesis of non-8-en-1-yl acetate from oct-7-en-1-ol by one-carbon homologation via nitrilation and DIBAL reduction according to an embodiment of the disclosure. The non-8-en-1-yl acetate can be converted to Z8-12Ac (Oriental fruit moth; *Grapholita molesta*) and E8E10-12OH (Codling moth; *Cydia pomonella*) via subsequent metathesis steps. Such steps are described, for example, WO 2017/087710 and WO 2018/150379.

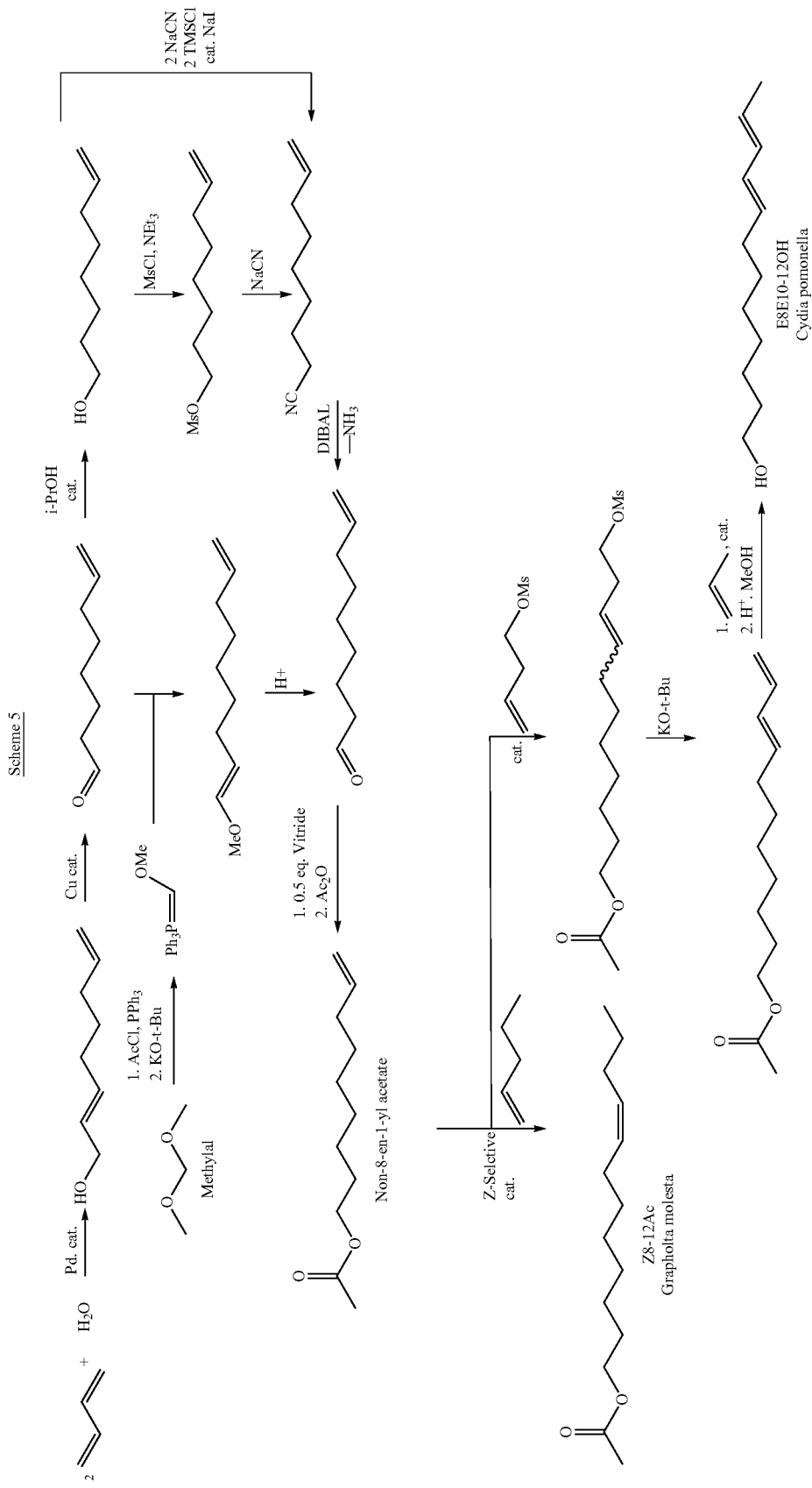

E. Epoxide Homologation

In some embodiments, the $C_4$-$C_{17}$ alkene reactant is an alkenyl Grignard reagent, the homologation reagent is an epoxide, and the $C_6$-$C_{18}$ alkene product is an alkenol. The $C_4$-$C_{17}$ alkene reactant may be, for example, a compound according to Formula I wherein $R^1$ is a Grignard moiety —MgBr or —MgCl; the homologation reagent may be ethylene oxide; and the $C_6$-$C_{18}$ alkene product may be an alkenol according to Formula IIId:

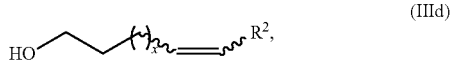
(IIId)

as described above, which can be acylated to form an alkenol ester, e.g., an alkenol ester according to Formula IX. A metathesis catalyst can then be used in the reaction of an alkenol ester according to Formula IX with a $C_2$-$C_{10}$ alkene according to Formula IV, providing a metathesis product according to Formula VII.

Scheme 6 shows the synthesis of dodec-11-en-1-ol via two-carbon homologation of dec-9-en-1-ol using ethylene oxide according to a non-limiting embodiment of the disclosure.

homologation reaction is typically conducted at temperatures ranging from around −10° C. to about 80° C. for a period of time sufficient to form the alkenol (e.g., from about 1 hour to about 18 hours), depending on the particular epoxide homologation reagent and the Grignard reagent used in the reaction.

F. Orthoester/Haloacetal Homologation

In some embodiments, the $C_4$-$C_{17}$ alkene reactant is an alkenyl Grignard reagent, the homologation reagent is an orthoester or a haloacetal, and the $C_6$-$C_{18}$ alkene product is an alkenal. The $C_4$-$C_{17}$ alkene reactant may be, for example, a compound according to Formula I wherein $R^1$ is a Grignard moiety —MgBr or —MgCl; the homologation reagent may be an orthoester having the formula $CH(OR^{7a})_3$; and the $C_6$-$C_{18}$ alkene product may be an acetal according to Formula XIII:

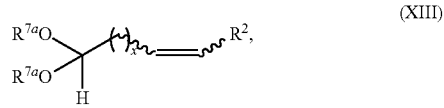
(XIII)

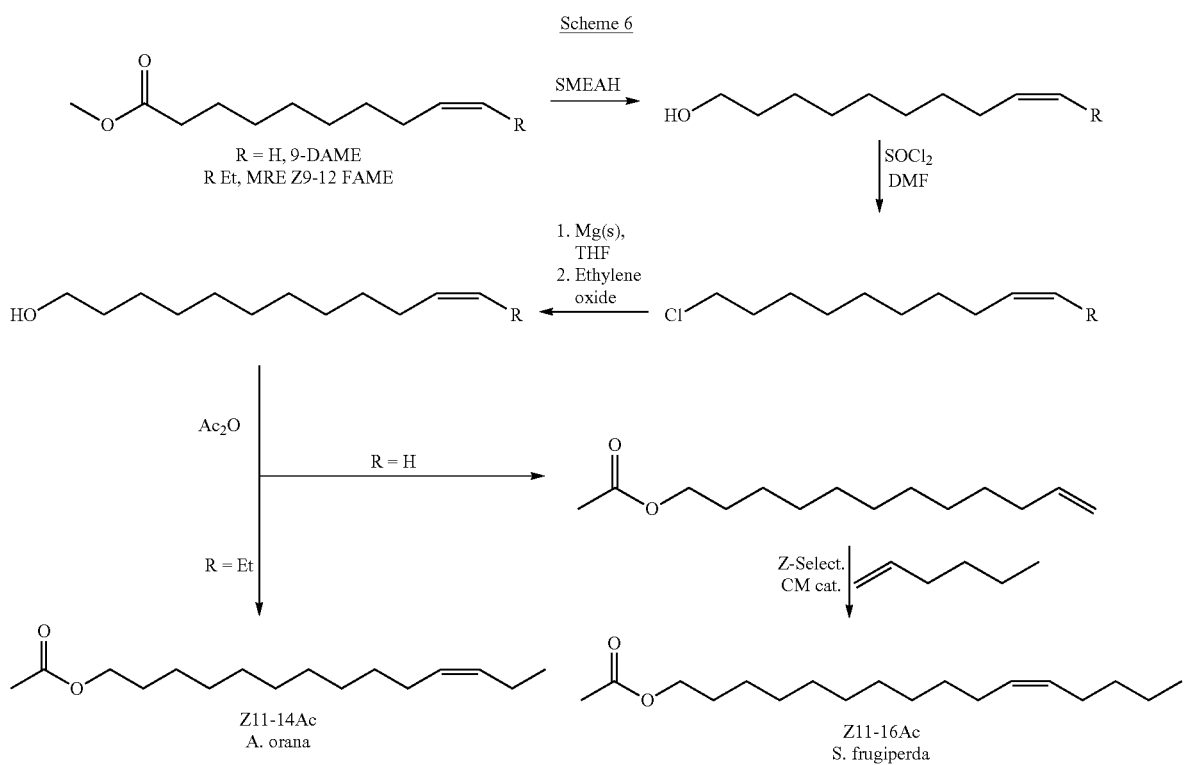
Scheme 6

Z11-14Ac
A. orana

Z11-16Ac
S. frugiperda

Typically, 0.5-3.5 molar equivalents of the epoxide homologation reagent with respect to the $C_4$-$C_{17}$ alkene reactant will be used. For example, 0.8-2.0 molar equivalents of the epoxide homologation reagent or 0.9-1.1 molar equivalents of the epoxide homologation reagent can be used. In some embodiments, around 0.8, 0.9, 1.0, 1.1, 1.2, 1.3, 1.4, or 1.5 molar equivalents of the epoxide homologation reagent (e.g., ethylene oxide) with respect to the $C_4$-$C_{17}$ alkene reactant (e.g., an alkenyl magnesium bromide) is used to form the alkenol homologation product. The wherein each $R^{7a}$ is an independently selected $C_{1-6}$ alkyl group. Each $R^{7a}$ may independently be, for example, methyl, ethyl, n-propyl, isopropyl, n-butyl, isobutyl, sec-butyl, tert-butyl, n-pentyl, branched pentyl, n-hexyl, or branched hexyl. In some embodiments, each $R^{7a}$ is methyl.

Acetals according to Formula XIII may then be subjected to acidic hydrolysis to provide alkenals according to Formula XIV:

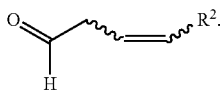

(XIV)

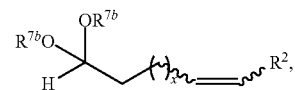

(XVI)

Scheme 7 shows the synthesis of (Z)-tetradec-11-enal (Z11-16Ald) and (Z)-hexadec-11-en-1-yl acetate (Z11-16Ac), beginning with the chlorination of (Z)-tetradec-9-en-1-ol (Z9-14OH). Z9-14OH can be prepared via cross-metathesis of methyl dec-9-enoate and hex-1-ene and reduction of the resulting methyl (Z)-tetradec-9-enoate as described, for example, in WO 2017/087710. The resulting chloride is reacted with magnesium metal to generate the corresponding Grignard reagent, which is then coupled with 2-bromo-1,1-dimethoxyethane to yield Z11-16Ald. The aldehyde can then be reduced and acetylated to provide Z11-16Ac.

wherein X is chloro, bromo, or iodo, and each $R^{7a}$ is an independently selected $C_{1-6}$ alkyl group. Each $R^{7a}$ may independently be, for example, methyl, ethyl, n-propyl, isopropyl, n-butyl, isobutyl, sec-butyl, tert-butyl, n-pentyl, branched pentyl, n-hexyl, or branched hexyl. In some embodiments, each $R^{7a}$ is methyl.

Acetals according to Formula XVI may then be subjected to acidic hydrolysis to provide alkenals according to Formula XII:

Scheme 7

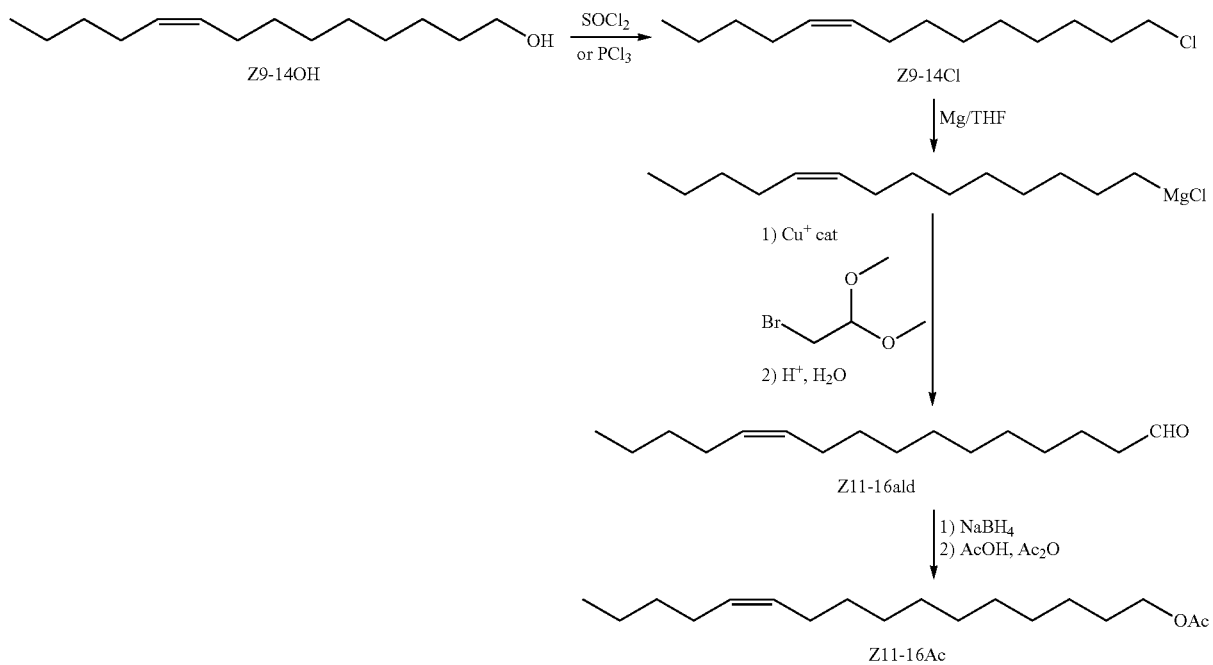

In some embodiments, the $C_4$-$C_{17}$ alkene reactant is a compound according to Formula I wherein $R^1$ is a Grignard moiety —MgBr or —MgCl; the homologation reagent is a haloacetal according to Formula XV

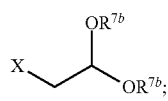

(XV)

and the $C_6$-$C_{18}$ alkene product is an acetal according to Formula XVI:

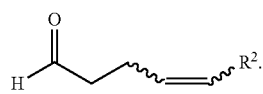

(XII)

Scheme 8 shows the synthesis of (Z)-dodec-8-en-1-yl acetate (Z8-12Ac) from oct-7-en-1-yl acetate (7-OAc). Z-selective cross-metathesis of 7-OAc and commercially available pent-1-ene followed by hydrolysis yields (Z)-undec-7-en-1-ol (Z7-11OH). The resulting alcohol is converted into the corresponding chloride and then reacted with magnesium metal to generate the Grignard reagent. The Grignard is reacted with triethyl orthoformate to form (Z)-dodec-8-enal, which is reduced and acetylated to yield the desired Z8-12Ac.

Scheme 8

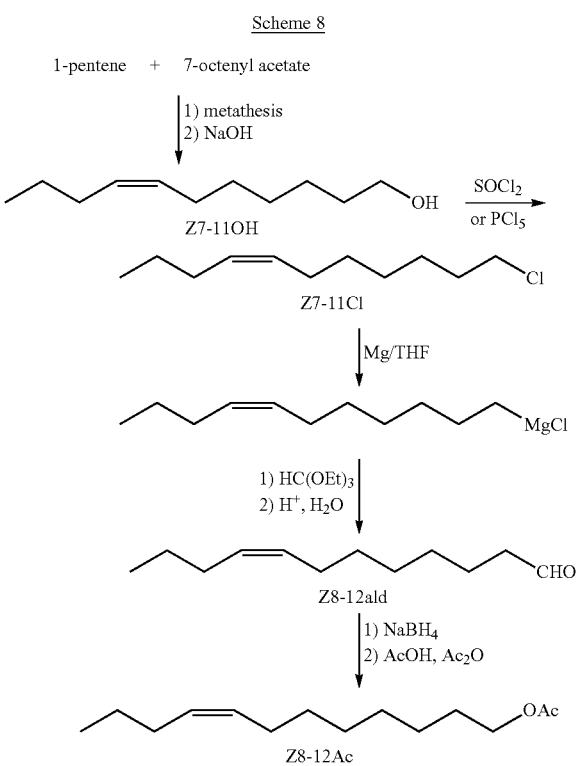

Typically, 0.5-3.5 molar equivalents of the haloacetal or orthoester homologation reagent with respect to the $C_4$-$C_{17}$ alkene reactant will be used. For example, 0.8-2.0 molar equivalents of the haloacetal or orthoester homologation reagent or 0.9-1.1 molar equivalents of the haloacetal or orthoester homologation reagent can be used. In some embodiments, around 0.8, 0.9, 1.0, 1.1, 1.2, 1.3, 1.4, or 1.5 molar equivalents of a haloacetal homologation reagent (e.g., bromoacetaldehyde dimethyl acetal) or an orthoester homologation reagent (e.g., trimethyl orthoformate) with respect to the $C_4$-$C_{17}$ alkene reactant (e.g., an alkenyl magnesium bromide) is used to form the homologation product. The homologation reaction is typically conducted at temperatures ranging from around $-10°$ C. to about $80°$ C. for a period of time sufficient to form the homologation product (e.g., from about 1 hour to about 18 hours), depending on the particular epoxide homologation reagent and the Grignard reagent used in the reaction. Alkenals according to Formula XII and Formula XIV can be further reduced to form the corresponding alkenols, which can be further acylated to form the corresponding alkenol esters (e.g., alkenyl acetates). Metathesis steps as described above, can be performed before or after such steps. In some embodiments, the alkenal(s), alkenol(s), and/or alkenyl acetate(s) prepared in this manner are insect pheromone(s).

G. Haloalkyl Ether Homologation

In some embodiments, the $C_4$-$C_{17}$ alkene reactant is an alkenyl Grignard reagent, the homologation reagent is a haloalkyl ether, and the $C_6$-$C_{18}$ alkene product is an alkenyl ether. The $C_4$-$C_{17}$ alkene reactant may be, for example, a compound according to Formula I wherein $R^1$ is a Grignard moiety —MgBr or —MgCl; the homologation reagent may be a haloalkyl ether according to Formula XVII

and the $C_6$-$C_{18}$ alkene product may be a protected alkenol according to Formula XVI.

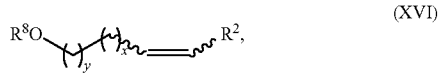

wherein X is chloro, bromo, or iodo, $R^8$ is alcohol protecting group, and subscript y is 1 or 2. Examples of suitable protecting groups include, but are not limited to, methyl ethers, a substituted methyl ethers, an ethyl ethers, a substituted ethyl ethers, a benzyl ethers, a substituted benzyl ether, and a silyl ethers. In some embodiments, protecting group $R^8$ is a substituted methyl ether. For example, $R^8$ can be methoxymethyl; methylthiomethyl; (phenyldimethylsilyl)-methoxymethyl; benzyloxymethyl; p-methoxybenzyloxymethyl; [(3,4-dimethoxybenzyl)oxy]methyl; p-nitrobenzyloxymethyl; o-nitrobenzyloxymethyl; [(R)-1-(2-nitrophenyl)ethoxy]methyl; (4-methoxyphenoxy)methyl; guaiacolmethyl; {(p-phenylphenyl)oxy}methyl; t-butoxymethyl; siloxymethyl; 2-methoxyethoxymethyl; 2-cyanoethoxymethyl; bis(2-chloroethoxy)methyl; 2,2,2-trichloroethoxymethyl; 2-(trimethylsilyl)ethoxymethyl; menthoxymethyl; O-bis(2-acetoxyethoxy)methyl; tetrahydropyranyl; fluorine-substituted tetrahydropyranyl; 3-bromotetrahydro-pyranyl; tetrahydrothiopyranyl; 1-methoxycyclohexyl; 4-methoxytetrahydropyranyl; 4-methoxytetrahydrothiopyranyl; 4-methoxytetrahydrothiopyranyl S,S-dioxide; 1-[(2-chloro-4-methyl)phenyl]-4-methoxypiperidin-4-yl; 1-(2-fluorophenyl)$_{0-4}$-methoxypiperidin-4-yl; 1-(4-chlorophenyl)$_{0-4}$-methoxypiperidin-4-yl; 1,4-dioxan-2-yl; tetrahydrofuranyl; tetrahydrothiofuranyl; or 2.3.3a,4,5,6,7,7a-octahydro-7,8,8-trimethyl-4,7-methanobenzofuran-2-yl. Protecting group $R^8$ can be removed via any suitable method, including those described by Green and Wuts (*Protective Groups in Organic Synthesis*, 4$^{th}$Ed. 2007, Wiley-Interscience, New York). The resulting alkenol may then be used in any combination of oxidation, acylation, or metathesis steps as described above. In some embodiments, the haloalkyl ether is a compound according to Formula XVII wherein X is chloro, subscript y is 1, and R is methoxymethyl.

Scheme 9 shows the synthesis of (Z)-tetradec-11-en-1-yl acetate (Z11-14Ac) and (Z)-hexadec-11-en-1-yl acetate (Z11-16Ac), starting with the chlorination of undec-10-en-1-ol (10-11OH). 10-11OH can be prepared via reduction of undec-10-enoic acid which is obtained commercially through pyrolysis of castor oil. The resulting chloride is reacted with magnesium metal to generate the corresponding Grignard reagent which is then coupled with chloro(methoxymethoxy)methane to yield (dodec-11-en-1-yloxy)(methoxy)methane. After conversion of the ether to the corresponding acetate, Z-selective metathesis with either but-1-ene or hex-1-ene yields Z11-14Ac and Z11-16Ac, respectively.

Scheme 9

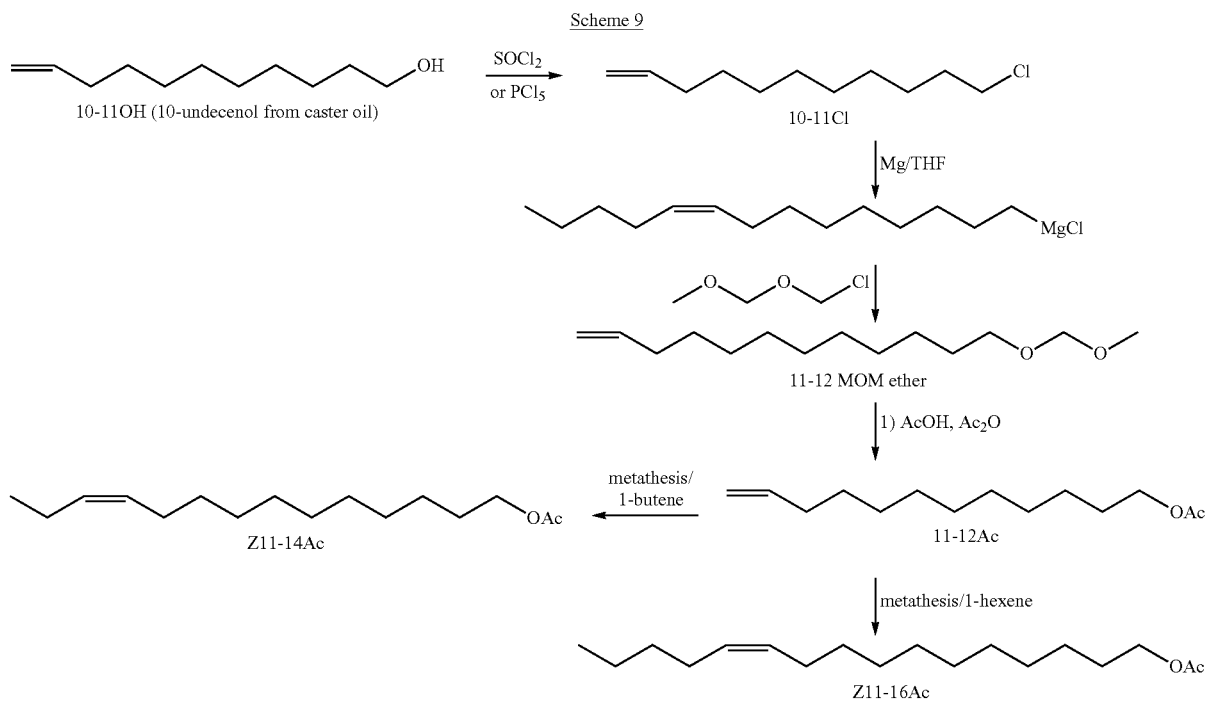

Typically, 0.5-3.5 molar equivalents of the haloalkylether homologation reagent with respect to the $C_4$-$C_{17}$ alkene reactant will be used. For example, 0.8-2.0 molar equivalents of the haloalkylether homologation reagent or 0.9-1.1 molar equivalents of the haloalkyl ether homologation reagent can be used. In some embodiments, around 0.8, 0.9, 1.0, 1.1, 1.2, 1.3, 1.4, or 1.5 molar equivalents of the haloalkyl ether homologation reagent (e.g., chloro(methoxymethoxy)methane) with respect to the $C_4$-$C_{17}$ alkene reactant (e.g., an alkenyl magnesium chloride) is used to form the protected alkenol homologation product. The homologation reaction is typically conducted at temperatures ranging from around −10° C. to about 80° C. for a period of time sufficient to form the homologation product (e.g., from about 1 hour to about 18 hours), depending on the particular epoxide homologation reagent and the Grignard reagent used in the reaction.

H. Formaldehyde Homologation

In some embodiments, the $C_4$-$C_{17}$ alkene reactant is an alkenyl Grignard reagent, the homologation reagent is formaldehyde or a formaldehyde precursor, and the $C_6$-$C_{18}$ alkene product is an alkenol. The $C_4$-$C_{17}$ alkene reactant may be, for example, a compound according to Formula I wherein $R^1$ is a Grignard moiety —MgBr or —MgCl; the homologation reagent may be formaldehyde, paraformaldehyde, or 1,3,5-trioxane; and the $C_6$-$C_{18}$ alkene product may be an alkenol according to Formula XVIII.

(XVIII)

which can be further oxidized to from the corresponding alkenals or acylated to form the corresponding alkenol esters (e.g., alkenyl acetates). Metathesis steps as described above, can be performed before or after such steps. In some embodiments, the alkenal(s), alkenol(s), and/or alkenyl acetate(s) prepared in this manner are insect pheromone(s).

Scheme 10 shows the synthesis of (Z)-dodec-8-en-1-yl acetate (Z8-12Ac) starting from oct-7-en-1-yl acetate (7-OAc), starting with the Z-selective cross-metathesis of 7-OAc and commercially available pent-1-ene. The reaction product is hydrolyzed to yield (Z)-undec-7-en-1-ol (Z7-11OH), and the resulting alcohol is converted into the corresponding chloride and reacted with magnesium metal to generate the Grignard reagent. The Grignard is reacted with formaldehyde or a surrogate such as 1,3,5-trioxane to yield (Z)-dodec-8-en-1-ol which is acetylated to yield the desired Z8-12Ac.

Scheme 10

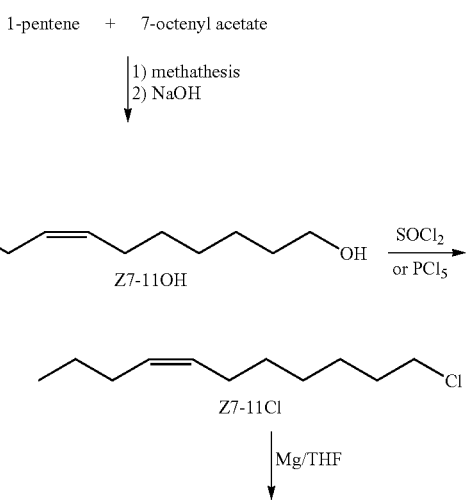

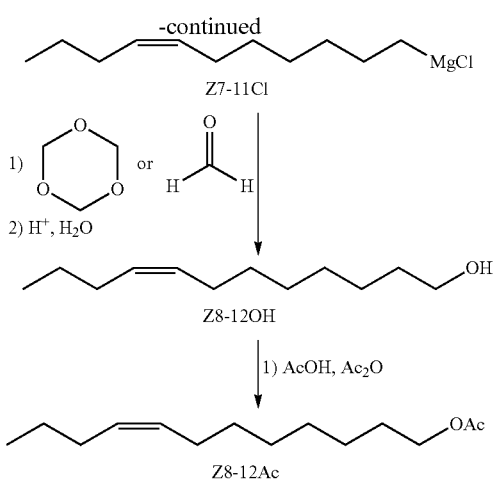

Typically, 0.5-3.5 molar equivalents of the formaldehyde or formaldehyde precursor with respect to the $C_4$-$C_{17}$ alkene reactant will be used. For example, 0.8-2.0 molar equivalents of the formaldehyde/formaldehyde precursor or 0.9-1.1 molar equivalents of the formaldehyde/formaldehyde precursor can be used. In some embodiments, around 0.8, 0.9, 1.0, 1.1, 1.2, 1.3, 1.4, or 1.5 molar equivalents of a formaldehyde precursor (e.g., 1,3,5-trioxane) with respect to the $C_4$-$C_{17}$ alkene reactant (e.g., an alkenyl magnesium chloride) is used to form the homologation product. The homologation reaction is typically conducted at temperatures ranging from around −10° C. to about 80° C. for a period of time sufficient to form the homologation product (e.g., from about 1 hour to about 18 hours), depending on the particular homologation reagent and the Grignard reagent used in the reaction.

III. Pheromone Compositions and Uses Thereof

As described above, a number of the alkene products obtained via the methods of the present disclosure can be used as insect pheromones or pheromone precursor materials. Pheromones prepared according to the methods described herein can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; and mixtures thereof. Baits or feeding stimulants can also be added to the carrier.

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices.

Pheromone compositions can contain other pheromones or attractants provided that the other compounds do not substantially interfere with the activity of the composition. The pheromone compositions can also include insecticides. Examples of suitable insecticides include, but are not limited to, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, and mixtures thereof.

Pheromone compositions can be used in conjunction with a dispenser for release of the composition in a particular environment. Any suitable dispenser known in the art can be used. Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

A variety of pheromones can be prepared according to the methods of the invention and formulated as described above. For example, the methods can be used to prepare the Asiatic rice borer (*Chilo suppressalis*) sex pheromone, (Z)-octadec-13-enal (Z13-18Ald). This sex pheromone can be used in conjunction with a sustained pheromone release device having a polymer container containing a mixture of the pheromone and a fatty acid ester (such as a sebacate, laurate, palmitate, stearate or arachidate ester) or a fatty alcohol (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol). The polymer container can be a tube, an ampule, or a bag made of a polyolefin or an olefin component-containing copolymer. Sex pheromones of other pest insects such as the summer fruit *tortrix* (*Adoxophyes orana*), the codling moth (*Cydia pomonella*), the cotton bollworm (*Helicoverpa armigera*), fall army worm (*Spodoptera frugiperda*), oriental fruit moth (*Grapholita molesta*) and leaf roller (Tortricidae) can be used in this type of sustained pheromone release device. The sex pheromones typically include one or more aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like) and/or one or more aliphatic aldehyde compounds having from 10 to 16 carbon atoms (e.g., 7-hexadecenal, 11-hexadecenal, 13-octadecenal, and the like).

Pheromones prepared according to the methods described herein, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps can be colored brightly, to provide additional attraction for the insects.

The trap is positioned in an area infested (or potentially infested) with insects. Generally, the trap is placed on or close to a tree or large plant and the pheromone attracts the insects to the trap. The insects can then be caught, immobilized and/or killed within the trap, for example, by the killing agent present in the trap.

Pheromones prepared according to the methods described herein can also be used to disrupt mating. Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

Insect populations can be surveyed or monitored by counting the number of insects in a target area (e.g., the number of insects caught in a trap). Inspection by a horticulturist can provide information about the life stage of a population. Knowing where insects are, how many of them there are, and their life stage enables informed decisions to be made as to where and when insecticides or other treatments are warranted. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

IV. Examples

Example 1. Preparation of ethyl (Z)-2-cyanotetradec-9-enoate

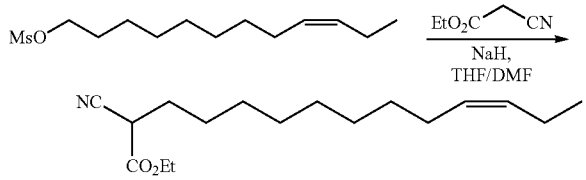

In a reactor cooled to 0° C. under an inert atmosphere, ethyl cyanoacetate (approx. 3 mol eq.) is added to a suspension of NaH (approx. 1.5 mol eq.) in a mixture of anhydrous THF/DMF. The mixture is stirred for 30 minutes after the addition is complete and then warmed to ambient temperature. (Z)-Dodec-9-en-1-yl methanesulfonate (1 mol eq.) and a catalytic amount of anhydrous sodium iodide are added at room temperature. The mixture is heated to reflux until the reaction is complete. The mixture is quenched with a saturated $NH_4Cl$ solution. The organic layer and any extracts required are combined and purified by distillation, crystallization or chromatography to yield ethyl (Z)-2-cyanotetradec-9-enoate.

Example 2. Preparation of (Z)-tetradec-11-enenitrile

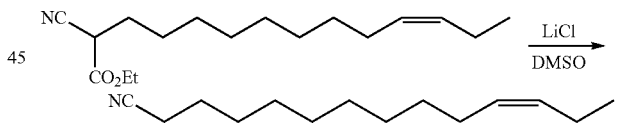

A vessel flask equipped with a stirrer and reflux condenser is charged with ethyl (Z)-2-cyanotetradec-9-enoate (1 mol eq.), a 100:1 mixture of dimethylsulfoxide/water and lithium chloride (approx. 2 mol eq.) The solution is heated to reflux until the reaction is complete. The reaction mixture is washed with water and purified by distillation, crystallization or chromatography to yield (Z)-tetradec-11-enenitrile.

Example 3. Preparation of (Z)-tetradec-11-enal

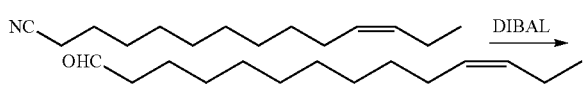

To an approx. −70° C. solution of (Z)-tetradec-11-enenitrile (1 mol eq.) in an aliphatic solvent is added diisobutylaluminum hydride (DIBAL; approx. 1 mol eq.) at such a rate that the temperature of the reaction mixture does not exceed −70° C. After the addition is complete the reaction mixture is stirred until complete consumption of the nitrile substrate is observed. The reaction mixture is warmed to ambient temperature and quenched by the addition of excess aqueous hydrochloric acid. The aqueous layer is separated and the organic layer is further extracted with water until the wash water has a neutral pH. The organic layer is distilled to yield (Z)-tetradec-11-enal.

Example 4. Preparation of (Z)-tetradec-11-en-1-yl Acetate

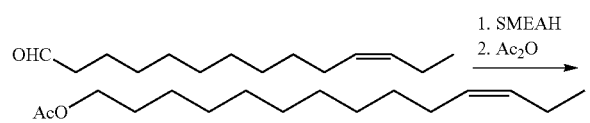

Under an inert atmosphere, a vessel is charged with (Z)-tetradec-11-enal (1 mol eq.) and toluene. After cooling to approx. 15° C., an approx. 70% solution of sodium bis(2-methoxyethoxy)aluminum hydride (approx. 0.5 mol eq.) is added at such a rate that the reaction temperature does not exceed approx. 15° C. When reduction of the aldehyde is complete the reaction mixture is quenched with an excess of aqueous sulfuric acid. The aqueous layer is separated, and the organic layer is washed with water until the wash water has a neutral pH. The solution is dried by azeotropic distillation with toluene and then cooled to approx. 60° C. A catalytic amount of anhydrous sodium acetate is added. Then acetic anhydride (approx. 1.2 eq. intermediate) is added at such a rate that the temperature of the reaction mixture does not exceed 70° C. When the reaction is complete, the reaction mixture is cooled to ambient temperature and quenched with water. The aqueous layer is separated, and the organic layer is purified by distillation to yield (Z)-tetradec-11-en-1-yl acetate.

Example 5. Preparation of Non-8-enenitrile

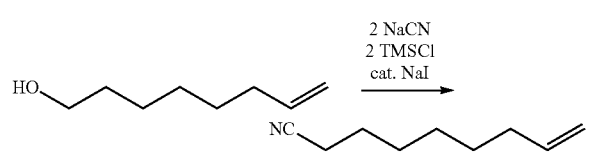

A vessel is charged with oct-7-en-1-ol (1 mol eq), 1:1 v/v acetonitrile/DMF (excess), sodium cyanide (2 mol eq.), a catalytic amount of sodium iodide and chlorotrimethylsilane under an inert atmosphere at ambient temperature. The mixture is then heated to approx. 60° C. until complete consumption of the alcohol substrate is observed. The reaction mixture is quenched by the addition of water. The aqueous layer is separated and the organic washed with additional water, if necessary. The organic layer is purified by distillation to yield non-8-enenitrile.

Example 6. Preparation of Non-9-enal

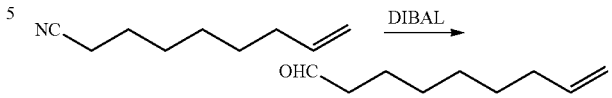

To an approx. −70° C. solution of non-9-enenitrile (1 mol eq.) in an aliphatic solvent is added diisobutylaluminum hydride (DIBAL; approx. 1 mol eq.) at such a rate that the temperature of the reaction mixture does not exceed approx. −70° C. After the addition is complete the reaction mixture is stirred until complete consumption of the nitrile substrate is observed. The reaction mixture is warmed to ambient temperature and quenched by the addition excess aqueous hydrochloric acid. The aqueous layer is separated and the organic layer further extracted with water until the wash water has a neutral pH. The organic layer is distilled to yield non-9-enal.

Example 7. Preparation of Non-8-en-1-yl Acetate

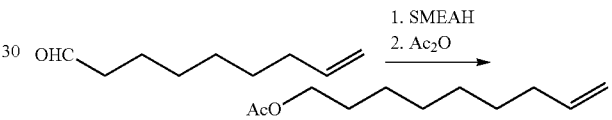

A vessel is charged with non-8-enal (1 mol eq.) and toluene. After cooling to approx. 15° C., an approx. 70% solution of sodium bis(2-methoxyethoxy)aluminum hydride (approx. 0.5 mol eq.) is added at such a rate that the reaction temperature does not exceed approx. 15° C. When reduction of the aldehyde is complete, the reaction mixture is quenched with an excess of aqueous sulfuric acid. The aqueous layer is separated, and the organic layer is washed with water until the wash water has a neutral pH. The solution is dried by azeotropic distillation with toluene and then cooled to approx. 60° C. A catalytic amount of anhydrous sodium acetate is added. Then acetic anhydride (approx. 1.2 eq. relative to alcohol intermediate) is added at such a rate that the temperature of the reaction mixture does not exceed 70° C. When the reaction is complete, the reaction mixture is cooled to ambient temperature and quenched with water. The aqueous layer is separated and the organic layer purified by distillation to yield non-8-en-1-yl acetate.

Example 8. Preparation of (Z)-dodec-8-en-1-yl Acetate

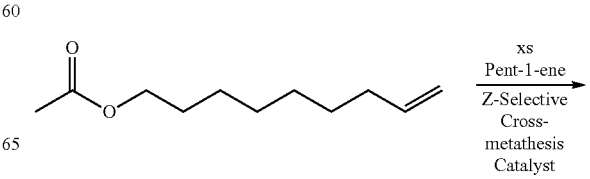

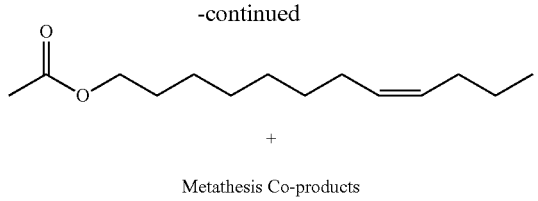

+

Metathesis Co-products

An excess of pent-1-ene and non-8-en-1-yl acetate are combined in a vessel and pretreated, if necessary. To the reaction mixture is added a catalytic amount of a Z-selective cross-metathesis catalyst, e.g., a catalyst according to Formula LII as described above. Evolution of ethylene is observed and this co-product is removed using a sparge of an inert gas. Once the reaction is complete, the reaction mixture is quenched and then purified by fractional distillation to yield (Z)-dodec-8-en-1-yl acetate.

Example 9. Preparation of (Z)-tetradec-11-en-1-yl Acetate

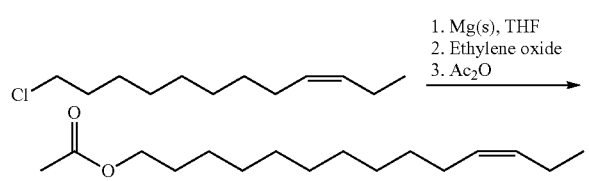

A mixture of (Z)-1-chlorododec-9-ene, THF, and excess magnesium is heated to reflux. The mixture is refluxed until complete consumption of the alkenyl chloride is observed. The mixture is then cooled to 0° C., and an excess of ethylene oxide is bubbled through the solution after first being dried through a column of anhydrous calcium carbonate. When complete consumption of the alkenyl magnesium intermediate is observed the reaction mixture is quenched by the addition of aqueous hydrochloric acid. The organic layer is further washed with water and dried by azeotropic distillation with toluene. To the crude alcohol intermediate is added a catalytic amount of anhydrous sodium acetate. The mixture is heated to approx. 60° C. and then acetic anhydride (approx. 1.2 eq. relative to crude alcohol intermediate) is added at such a rate that the temperature of the reaction mixture does not exceed 70° C. When the reaction is complete, the reaction mixture is cooled to ambient temperature and quenched with water. The aqueous layer is separated and the organic layer purified by distillation to yield (Z)-tetradec-11-en-1-yl acetate.

Example 10. Synthesis of 9-decenyl-O-mesylate

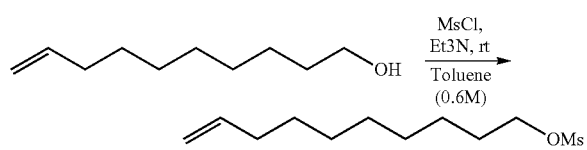

To a mixture of 9-decen-1-ol (0.918 g, 5.87 mmol) and Et₃N (0.98 mL, 7.05 mmol) in toluene (10 mL, 0.6M) was slowly added methanesulfonyl chloride (0.50 mL, 6.46 mmol) at 0° C. The mixture was stirred overnight while allowing the temperature to reach rt. After diluting the mixture with 10 mL of hexane and 10 mL of water, the organic phase was washed with 1N HCl (~10 mL), water, saturated NaHCO₃, brine; dried over MgSO₄; and concentrated under vacuum. Conversion to the product was determined as ~100% by GC analysis. The product was used without any further purification for the next reaction.

Example 11. Synthesis of 9-decenyl Chloride with Cyanuric Chloride

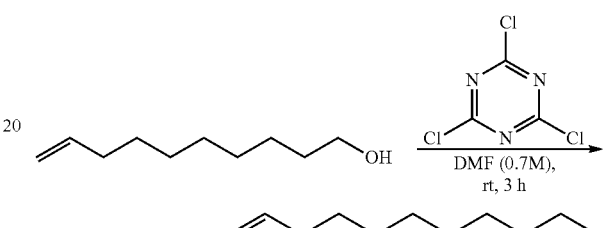

Anhydrous DMF (40 mL) was added to cyanuric chloride at rt in an inert atmosphere and the mixture was stirred at rt. The clear solution became a beige suspension in 10 min. After 30 min, 9-decen-1-ol (4.38 g, 28.03 mmol) was slowly added to the mixture at 0° C. The mixture was stirred at rt for another 3 h to complete chlorination. Saturated NaHCO₃ aqueous solution (20 mL) was carefully added to the mixture. After diluting the mixture with hexane, the organic phase was separated; washed with water and brine; dried over MgSO₄, and concentrated under vacuum to give 4.28 g of the product as colorless liquid. Conversion to 9-decenyl chloride was determined as 100% by GC analysis.

Example 12. Synthesis of 9-decenyl Chloride with Thionyl Chloride

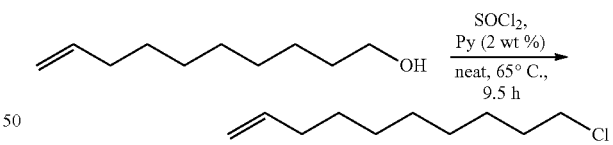

Thionyl chloride (4.1 mL) was slowly added to 9-decen-1-ol (8.08 g) at rt in an inert atmosphere followed by the addition of a catalytic amount of pyridine (0.17 mL). HCl gas that evolved over the courses of the reaction was neutralized by bubbling through NaOH solution. After stirring the mixture at 65° C. for 9.5 h, the extent of chlorination was determined to be ~98% by GC analysis. Hexane (10 mL) and water (10 mL) were carefully added to the reaction flask. The organic phase was separated and washed with water and saturated NaHCO₃ and brine. Drying the solution over MgSO₄ followed by concentration under vacuum gave 10.38 g of crude product. Distillation using a Kugelrohr apparatus purified the product to have 8.05 g of 9-decenyl chloride as a colorless liquid (89%, as determined by GC).

Example 13. Dimethyl Malonate Substitution of 9-decenyl-O-mesylate

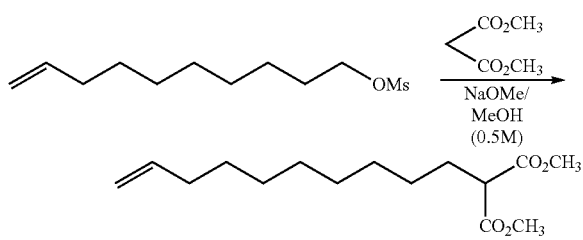

To a mixture of 9-decen-O-mesylate (1.0 eq.) and dimethyl malonate (2.0 eq.) in MeOH (0.5M) was slowly added sodium methoxide (2.0 eq.) at rt. The mixture was stirred at 40° C. for 21 h. Conversion to the target compound via substitution reached 77.3% as determined by GC.

Example 14. Dimethyl Malonate Substitution of 9-decenyl Chloride

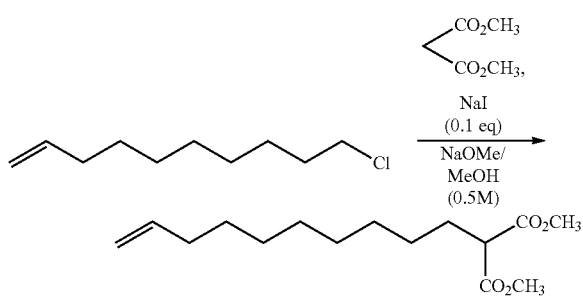

To a mixture of 9-decenyl chloride (1.0 eq.) and dimethyl malonate (1.5 eq.) in MeOH-DMF (0.5M, ratio of 3:5) was slowly added sodium methoxide (1.5 eq.) and sodium iodide (0.1 eq.) at rt. The mixture was stirred at 80° C. for 17 h. GC and GC-MS analysis indicated that the conversion of reached 74.4%.

Example 15. Two Carbon Homologation of 9-decenyl Chloride Via Grignard Reaction with Ethylene Oxide

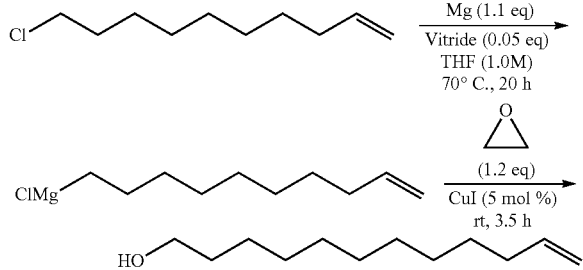

To magnesium turnings (40 mg) in a vial containing anhydrous THF (1.5 mL) was added Vitride solution (84 µL of 18 wt % in toluene, diluted from 70 wt % solution). After the mixture was stirred at 50° C. for 30 min, 9-decenyl chloride (0.262 g) was added. The reaction was continued with stirring at 70° C. for 20 h. A catalytic amount of copper iodide (14 mg) was added to the mixture at rt in an inert atmosphere followed by the addition of ethylene oxide at 0° C. (0.72 mL of 2.5~3.3 M solution in THF, purchased from Aldrich). The mixture was stirred at 0° C. for 30 min and continued with stirring at rt for 3.5 h. GC and GC-MS analysis identified that conversion of 9-decenyl chloride to 11-dodecen-1-ol via the Grignard reaction was 53.7%.

Example 16. Two Carbon Homologation of 9-decenyl Chloride Via Grignard Reaction with Bromoethyl Acetate

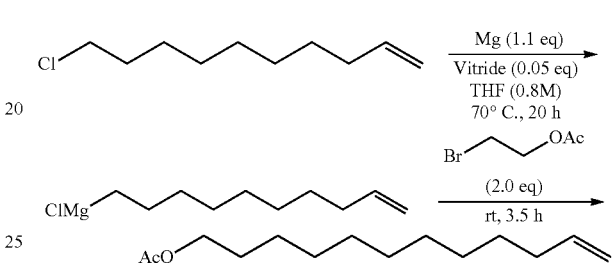

To magnesium turnings (40 mg) in a vial containing anhydrous THF (1.9 mL) was added Vitride solution (84 µL of 18 wt % in toluene, diluted from 70 wt % solution). After the mixture was stirred at 50° C. for 30 min, 9-decenyl chloride (0.262 g) was added. The reaction was continued with stirring at 70° C. for 20 h. 2-Bromoethyl acetate (0.33 mL) was added to the mixture at rt followed by stirring at rt for 3.5 h. GC and GC-MS analysis indicated that conversion of 9-decenyl chloride to the product via the Grignard reaction was 34.5%, along with the formation 1-decene as major by-product (51.0%).

Example 17. Preparation of (Z)-9-dodecenyl Chloride

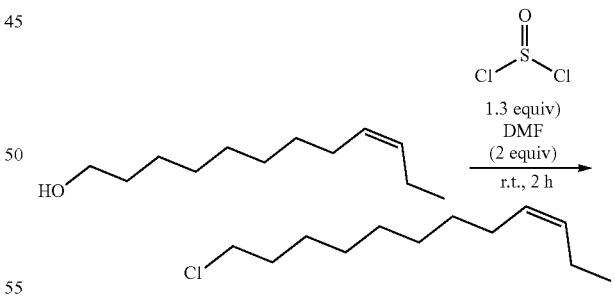

An oven dried 3-neck, 500 mL round bottom flask equipped with a large magnetic stir bar was charged with (Z)-9-dodecenol (72 g, 0.36 mol, 91% pure) and dimethylformamide (52 g, 0.71 mol). The solution was sparged with nitrogen (30 min.) followed by the dropwise addition (1 hour) of thionyl chloride (17 mL, 0.23 mol) via an addition funnel while vigorously stirring the reaction at 0° C. The reaction mixture reach a temperature of 37° C. then cooled back down to 0° C. while gradually turning to a thick yellow slurry. Stirring became difficult at lower temperatures so the second portion of thionyl chloride (17 mL, 0.23 mol) was added at ambient temperature while monitoring the exotherm to 40° C. Upon complete addition, the reaction was stirred at ambient temperature for 2 hours.

The crude material was transferred to a 2 L separatory funnel containing DI water (500 mL). A saturated solution of sodium bicarbonate was slowly added to the funnel until effervescence was no longer observed (~500 mL) followed by extraction of the crude mixture with hexane (300 mL). The organic phase was washed with saturated sodium bicarbonate solution (200 mL) followed by DI water (200 mL). The combined aqueous phases were then extracted with hexane (2×300 mL). Finally, the combined organic phases were dried over anhydrous sodium sulfate, filtered, and concentrated under reduced pressure (40° C., 70-30 Torr) to an orange colored liquid (85 g, quantitative yield, 86% pure). This material was subjected to flash distillation (pot temp: 103-119° C., head temp: 79-84° C., vacuum 150-80 mtorr), and the product was collected as a clear liquid (63 g, 76% yield, 87% pure).

Example 18. Preparation of (Z)-11-tetradecenol

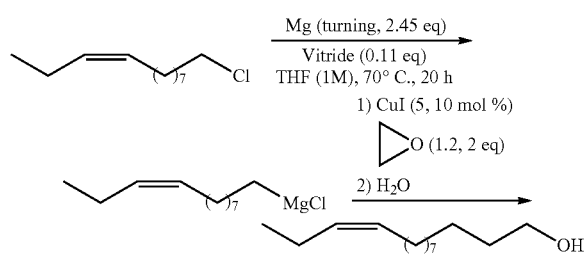

In a glovebox, four oven-dried 8 mL vials with a stir bar were each charged with magnesium turnings (60 mg, 2.5 mol), THF (1.0 mL) and Vitride (124 mg of 18 wt % sol. in toluene, 0.11 mol). Vials were capped and stirred at 50° C. for 1 hour. After cooling to r.t., (Z)-9-dodecenyl chloride (230 mg, 0.99 mol) was added to each vial and the Grignard reagents were allowed to form by stirring at 70° C. for 18 hours. Copper iodide (5 mol %×2 vials & 10 mol %×2 vials) was added at room temperature followed by the addition of ethylene oxide (1.2 eq.×2 vials & 2 eq.×2 vials) at 0° C. Reactions were stirred at ambient temperature for 4 hours. Reactions were then quenched with DI water (3 mL) and extracted with hexane (1 mL).

Example 19. Preparation of (Z)-11-tetradecenol Using Reverse Addition

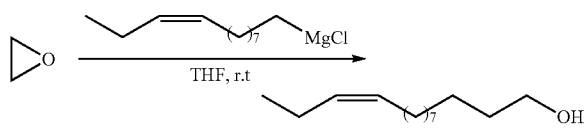

In a glovebox, an oven-dried 40 mL vial with a magnetic stir bar was charged with magnesium turnings (300 mg, 12.3 mol), THF (5.0 mL), and Vitride (605 mg of 18 wt % sol. in toluene, 0.11 eq). The vial was capped and stirred at 50° C. for 30 minutes. After cooling to r.t., (Z)-9-dodecenyl chloride (1.15 g, 4.9 mol) was added to the vial and the Grignard reagents were allowed to form by stirring at 70° C. for 18 hours. Copper iodide (93 mg, 10 mol %) was added to the reaction mixture at room temperature. The Grignard reagent was then added dropwise to a solution of ethylene oxide in THF (prepared by sparging ethylene oxide gas through THF, final weight 1.63 g in 5.0 mL of THF, 37 mol) while stirring at 0° C. The reaction was stirred at ambient temperature for 66 hours. Samples (0.2 mL) were taken at various time intervals (1, 4, 24, 26, and 66 hours), treated under work-up protocol and analyzed by GC.

Example 20. Preparation of (Z)-9-dodecenyl Magnesium Chloride with Vitride

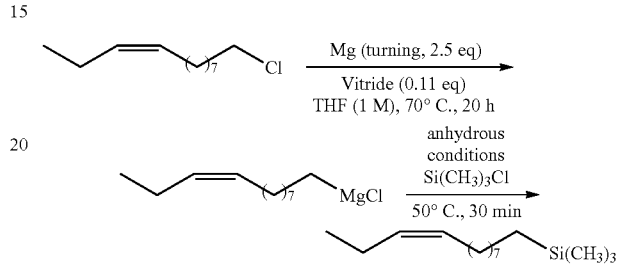

In a glovebox, an oven-dried 8 mL vial with a magnetic stir bar was charged with magnesium turnings (60 mg, 2.5 mol), THF (1.0 mL) and Vitride (124 mg of 18 wt % sol. in toluene, 0.11 mol). The vial was capped and stirred at 50° C. for 30 minutes. After cooling to r.t., (Z)-9-dodecenyl chloride (230 mg, 0.99 mol) was added to the vial and the Grignard reagent was allowed to form by stirring at 70° C. for 20 hours. A small sample (0.2 mL) was quenched with DI water and extracted with hexane. The top organic phase was then analyzed by GC. Another small sample (0.2 mL) was treated with excess chlorotrimethylsilane and stirred at 60° C. for 30 minutes under an inert atmosphere. The sample was analyzed by GC with no further work-up.

Example 21. Preparation of (Z)-9-dodecenyl Magnesium Chloride with DIBAL-H

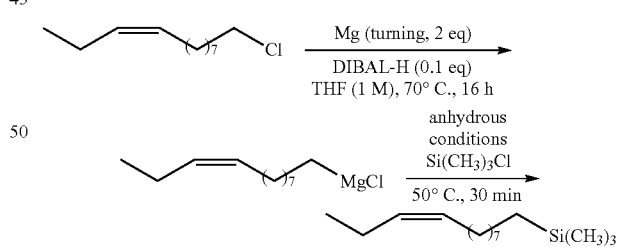

In a glovebox, an oven-dried 20 mL vial with a magnetic stir bar was charged with magnesium turnings (190 mg, 7.8 mol), THF (5.0 mL) and diisobutylaluminum hydride (61 mg, 0.1 eq). The vial was capped and stirred at 50° C. for 60 minutes. After cooling to r.t., (Z)-9-dodecenyl chloride (1.00 g, 4.3 mol) was added to the vial and the Grignard reagent was allowed to form by stirring at 70° C. for 16 hours. Small test samples (0.2 mL) were taken at 3 and 16 hours then treated with excess chlorotrimethylsilane (60° C. for 30 minutes under an inert atmosphere). The samples were analyzed by GC with no further work-up.

Example 22. Preparation of (Z)-9-dodecenyl Magnesium Chloride with Activated Magnesium Turnings

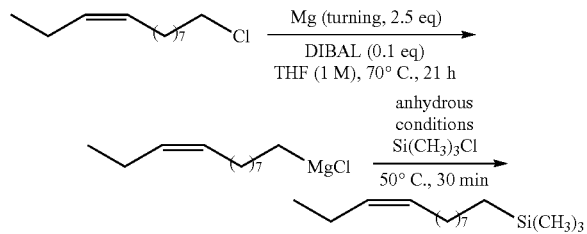

In a glovebox, an oven-dried 8 mL vial with a magnetic stir bar was charged with activated (40° C. under high vacuum for 60 hours) magnesium turnings (75 mg, 3.1 mol), THF (1.0 mL) and diisobutylaluminum hydride (18 mg, 0.1 eq). The vial was capped and stirred at 50° C. for 60 minutes. After cooling to r.t., (Z)-9-dodecenyl chloride (250 mg, 1.2 mol) was added to the vial and the Grignard reagent was allowed to form by stirring at 70° C. for 21 hours. Small test samples (0.2 mL) were taken at 0, 2 and 21 hours then treated with excess chlorotrimethylsilane (60° C. for 30 minutes under an inert atmosphere). The samples were analyzed by GC with no further work-up.

70 mL of 1-hexene was added to a flask containing 7.96 g of 8-nonen-1-ol inside glove box (10 eq. of 1-hexene to 8-nonen-1-ol). As soon as adding ruthenium catalyst to the mixture (C-633, 500 ppm to 8-nonen-1-ol; 45 ppm/double bond), the flask sealed with septum was taken out from glove box and heated at 30° C. $N_2$ was sparged over the reaction to remove ethylene. After 4.5 h, the reaction was quenched by adding ethylenediamine (1.3 mL, 70 eq. to the catalyst) and the mixture was stirred for another 1 hr at rt. The mixture was passed through a silica-gel plug with n-hexane, which removed the brown color and afforded a colorless liquid. Pure tridec-8-en-1-ol was obtained by flash distillation under high vacuum and the yield was 8.4 g (Z8-13OH, >98% purity, 93% Z-form confirmed by GC analysis). Some of purified tridec-8-en-1-ol was continued to the next step for acetylation; 2.4 g of pure tridec-8-en-1-ol was added to a flask followed by adding acetic anhydride (1.2 eq.) and sodium acetate (0.1 eq.). The mixture was stirred at 60° C. for 1 h. The mixture was washed with water, saturated $NaHCO_3$, and brine prior to drying over $Na_2SO_4$. Removal of solvent under reduced pressure provided 2 g of pure tridec-8-en-1-ol acetate (Z8-13Ac, >98% purity, 92% Z-form confirmed by GC analysis).

V. Exemplary Embodiments

Exemplary embodiments provided in accordance with the presently disclosed subject matter include, but are not limited to, the claims and the following embodiments:

1. A method for the preparation of a $C_6$-$C_{18}$ alkene product, the method comprising contacting a $C_4$-$C_{17}$ alkene reactant with a homologation reagent under conditions sufficient to form the $C_6$-$C_{18}$ alkene product.

2. The method of embodiment 1, wherein the homologation reagent is an epoxide, a 1,3-diester, a cyanoacetate, a cyanide salt, an orthoester, a haloacetal, a haloalkyl ether, formaldehyde, or a formaldehyde precursor.

3. The method of embodiment 1 or embodiment 2, comprising contacting a $C_6$-$C_{17}$ alkene reactant with the homologation reagent under conditions sufficient to form a $C_8$-$C_{18}$ alkene product.

4. The method of any one of embodiments 1-3, wherein the $C_6$-$C_{18}$ alkene product comprises a 7-unsaturated alkene, an 8-unsaturated alkene, a 9-unsaturated alkene, or an 11-unsaturated alkene.

5. The method of any one of embodiments 1-4, wherein the $C_4$-$C_{17}$ alkene reactant is an alkenyl Grignard reagent, an alkenyl sulfonate, or an alkenyl halide.

6. The method of any one of embodiments 1-5, wherein the $C_4$-$C_{17}$ alkene reactant is obtained from hept-6-en-1-ol, oct-7-en-1-ol, (Z)-undec-7-en-1-ol, (Z)-dodec-9-en-1-ol, (Z)-tetradec-9-en-1-ol, dec-9-en-1-ol, methyl dec-9-enoate, undec-10-en-1-ol, or (Z)-hexadec-11-en-1-ol.

7. The method of any one of embodiments 1-6, wherein the $C_4$-$C_{17}$ alkene reactant is an alkenyl halide or an alkenyl sulfonate, the homologation reagent is a 1,3-diester, and the $C_6$-$C_{18}$ alkene product is a 2-(alkenyl)malonate.

8. The method of embodiment 7, further comprising converting the 2-(alkenyl)malonate to an alkenoic acid.

9. The method of embodiment 8, further comprising esterifying the alkenoic acid to form an alkyl alkenoate.

10. The method of embodiment 9, further comprising contacting the alkyl alkenoate with a $C_2$-$C_{10}$ alkene in the presence of a metathesis catalyst under conditions sufficient to form an alkyl alkenoate metathesis product.

11. The method of embodiment 10, further comprising contacting the alkyl alkenoate metathesis product with a reducing agent under conditions sufficient to form an alkenol.

12. The method of embodiment 11, further comprising contacting the alkenol with an acylating agent under conditions sufficient to form an alkenol ester.

13. The method of embodiment 10, further comprising contacting the alkyl alkenoate metathesis product with a reducing agent under conditions sufficient to form an alkenal.

14. The method of embodiment 8, further comprising reducing the alkenoic acid to form an alkenol.

15. The method of embodiment 14, further comprising acylating the alkenol under conditions sufficient to form an alkenol ester.

16. The method of embodiment 15, further comprising contacting the alkenol ester with a $C_2$-$C_{10}$ alkene in the presence of a metathesis catalyst under conditions sufficient to form a metathesis product.

17. The method of any one of embodiments 1-6, wherein the $C_4$-$C_{17}$ alkene reactant is an alkenyl Grignard reagent, the homologation reagent is an epoxide, and the $C_6$-$C_{18}$ alkene product is an alkenol.

18. The method of embodiment 17, wherein the epoxide is ethylene oxide.

19. The method of embodiment 17 or embodiment 18, further comprising acylating the alkenol under conditions sufficient to form an alkenol ester.

20. The method of embodiment 19, further comprising contacting the alkenol ester with a $C_2$-$C_{10}$ alkene in the presence of a metathesis catalyst under conditions sufficient form a metathesis product.

21. The method of any one of embodiments 1-6, wherein the $C_4$-$C_{17}$ alkene reactant is an alkenyl halide or an alkenyl sulfonate, the homologation reagent is a cyanoacetate, and the $C_6$-$C_{18}$ alkene product is an alkyl (2-cyano)alkenoate.

22. The method of embodiment 21, further comprising decarboxylating the alkyl (2-cyano)alkenoate to form an alkenyl nitrile.

23. The method of any one of embodiments 1-6, wherein the $C_4$-$C_{17}$ alkene reactant is an alkenyl sulfonate or an alkenyl halide, the homologation reagent is a cyanide salt, and the $C_6$-$C_{18}$ alkene product is an alkenyl nitrile.

24. The method of embodiment 22 or embodiment 23, further comprising reducing the alkenyl nitrile to form an alkenal.

25. The method of embodiment 24, wherein the alkenal is an insect pheromone.

26. The method of embodiment 24, further comprising reducing the alkenal to form an alkenol.

27. The method of embodiment 26, further comprising acylating the alkenol under conditions sufficient to form an alkenol ester.

28. The method of embodiment 27, further comprising contacting the alkenol ester with a $C_2$-$C_{10}$ alkene in the presence of a metathesis catalyst under conditions sufficient to form a metathesis product.

29. The method of any one of embodiments 1-6, wherein the $C_4$-$C_{17}$ alkene reactant is an alkenyl Grignard reagent, the homologation reagent is a haloacetal or an orthoester, and the $C_6$-$C_{18}$ alkene product is an alkenal.

30. The method of embodiment 29, further comprising reducing the alkenal under conditions sufficient to form an alkenol.

31. The method of embodiment 30, further comprising acylating the alkenol under conditions sufficient to form an alkenol ester.

32. The method of any one of embodiments 1-6, wherein the $C_4$-$C_{17}$ alkene reactant is an alkenyl Grignard reagent, the homologation reagent is a haloalkyl ether, and the $C_6$-$C_{18}$ alkene product is an alkenyl ether.

33. The method of embodiment 32, further comprising converting the alkenyl ether to an alkenol.

34. The method of any one of embodiments 1-6, wherein the $C_4$-$C_{17}$ alkene reactant is an alkenyl Grignard reagent, the homologation reagent is formaldehyde or a formaldehyde precursor, and the $C_6$-$C_{18}$ alkene product is an alkenol.

35. The method of embodiment 33 or 34, further comprising acylating the alkenol under conditions sufficient to form an alkenol ester.

36. The method of any one of embodiments 12, 15, 19, 27, 31, and 35, wherein the alkenol ester is an alkenyl acetate.

37. The method of embodiment 36, wherein the alkenyl acetate is an insect pheromone.

38. The method of embodiment 13, wherein the alkenal is an insect pheromone.

39. The method of any one of embodiments 16, 20, and 28, wherein the alkenol ester is an alkenyl acetate and wherein the metathesis product is an insect pheromone.

40. An alkene product prepared according to the method of any one of embodiments 1-39.

41. An insect pheromone prepared from an alkene product according to embodiment 40.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for the preparation of a $C_6$-$C_{18}$ alkene product, the method comprising contacting a $C_4$-$C_{17}$ alkene reactant with a homologation reagent under conditions sufficient to form the $C_6$-$C_{18}$ alkene product, wherein the $C_6$-$C_{18}$ alkene product comprises a 7-unsaturated alkene, an 8-unsaturated alkene, a 9-unsaturated alkene, or an 11-unsaturated alkene, wherein the $C_4$-$C_{17}$ alkene reactant is an alkenyl Grignard reagent, an alkenyl sulfonate, or an alkenyl halide, and wherein the $C_6$-$C_{18}$ alkene product is not a benzyl ether.

2. The method of claim 1, wherein the homologation reagent is an epoxide, a 1,3-diester, a cyanoacetate, a cyanide salt, an orthoester, a haloacetal, a haloalkyl ether, formaldehyde, or a formaldehyde precursor.

3. The method of claim 1, comprising contacting a $C_6$-$C_{17}$ alkene reactant with the homologation reagent under conditions sufficient to form a $C_8$-$C_{18}$ alkene product.

4. The method of claim 1, wherein the $C_4$-$C_{17}$ alkene reactant is an alkenyl Grignard reagent, the homologation reagent is an epoxide, and the $C_6$-$C_{18}$ alkene product is an alkenol.

5. The method of claim 4, further comprising acylating the alkenol under conditions sufficient to form an alkenol ester, and optionally contacting the alkenol ester with a $C_2$-$C_{10}$ alkene in the presence of a metathesis catalyst under conditions sufficient form a metathesis product.

6. The method of claim 1, wherein the $C_4$-$C_{17}$ alkene reactant is an alkenyl halide or an alkenyl sulfonate, the homologation reagent is a 1,3-diester, and the $C_6$-$C_{18}$ alkene product is a 2-(alkenyl) malonate.

7. The method of claim 6, further comprising converting the 2-(alkenyl) malonate to an alkenoic acid.

8. The method of claim 7, further comprising esterifying the alkenoic acid to form an alkyl alkenoate.

9. The method of claim 8, further comprising contacting the alkyl alkenoate with a $C_2$-$C_{10}$ alkene in the presence of a metathesis catalyst under conditions sufficient to form an alkyl alkenoate metathesis product.

10. The method of claim 9, further comprising contacting the alkyl alkenoate metathesis product with a reducing agent under conditions sufficient to form an alkenol, optionally contacting the alkenol with an acylating agent under conditions sufficient to form an alkenol ester, and optionally contacting the alkyl alkenoate metathesis product with a reducing agent under conditions sufficient to form an alkenal.

11. The method of claim 7, further comprising reducing the alkenoic acid to form an alkenol, optionally acylating the alkenol under conditions sufficient to form an alkenol ester, and optionally contacting the alkenol ester with a $C_2$-$C_{10}$ alkene in the presence of a metathesis catalyst under conditions sufficient to form a metathesis product.

12. The method of claim 1, wherein:
the $C_4$-$C_{17}$ alkene reactant is an alkenyl halide or an alkenyl sulfonate, the homologation reagent is a cyanoacetate, and the $C_6$-$C_{18}$ alkene product is an alkyl (2-cyano) alkenoate, and the method further comprises decarboxylating the alkyl (2-cyano) alkenoate to form an alkenyl nitrile; or
the $C_4$-$C_{17}$ alkene reactant is an alkenyl sulfonate or an alkenyl halide, the homologation reagent is a cyanide salt, and the $C_6$-$C_{18}$ alkene product is an alkenyl nitrile.

13. The method of claim 12, further comprising reducing the alkenyl nitrile to form an alkenal.

14. The method of claim 13, further comprising reducing the alkenal to form an alkenol, optionally acylating the alkenol under conditions sufficient to form an alkenol ester, and optionally contacting the alkenol ester with a $C_2$-$C_{10}$ alkene in the presence of a metathesis catalyst under conditions sufficient to form a metathesis product.

15. The method of claim 1, wherein the $C_4$-$C_{17}$ alkene reactant is an alkenyl Grignard reagent, the homologation reagent is a haloacetal or an orthoester, and the $C_6$-$C_{18}$ alkene product is an alkenal.

16. The method of claim 15, further comprising reducing the alkenal under conditions sufficient to form an alkenol, and optionally acylating the alkenol under conditions sufficient to form an alkenol ester.

17. The method of claim 1, wherein:
the $C_4$-$C_{17}$ alkene reactant is an alkenyl Grignard reagent, the homologation reagent is a haloalkyl ether, and the $C_6$-$C_{18}$ alkene product is an alkenyl ether, and the method further comprises converting the alkenyl ether to an alkenol; or the $C_4$-$C_{17}$ alkene reactant is an alkenyl Grignard reagent, the homologation reagent is formaldehyde or a formaldehyde precursor, and the $C_6$-$C_{18}$ alkene product is an alkenol.

18. The method of claim 17, further comprising acylating the alkenol under conditions sufficient to form an alkenol ester.

* * * * *